United States Patent
Kothari et al.

(10) Patent No.: US 11,241,396 B2
(45) Date of Patent: *Feb. 8, 2022

(54) METHODS AND COMPOSITIONS FOR IMPROVING MICROVASCULAR FUNCTION, SUPPRESSING CYCLOOXYGENASE ACTIVITY, REDUCING PLATELET AGGREGATION AND INCREASING LEVELS OF RESVERATROL IN PLASMA

(71) Applicants: Shil Kothari, Fairfeild, CA (US); Gary Troxel, Fairfeild, CA (US)

(72) Inventors: Shil Kothari, Fairfeild, CA (US); Gary Troxel, Fairfeild, CA (US)

(73) Assignee: Gateway Health Alliances, Inc., Fairfield, CA (US)

( * ) Notice: Subject to any disclaimer, the term of this patent is extended or adjusted under 35 U.S.C. 154(b) by 1253 days.

This patent is subject to a terminal disclaimer.

(21) Appl. No.: 14/924,712

(22) Filed: Oct. 28, 2015

(65) Prior Publication Data

US 2017/0119894 A1   May 4, 2017

(51) Int. Cl.
| | | |
|---|---|---|
| *A61K 31/195* | (2006.01) | |
| *A61K 31/05* | (2006.01) | |
| *C07C 15/18* | (2006.01) | |
| *A61K 47/54* | (2017.01) | |

(52) U.S. Cl.
CPC .......... *A61K 31/05* (2013.01); *A61K 47/542* (2017.08); *C07C 15/18* (2013.01)

(58) Field of Classification Search
CPC .................. A61K 47/48038; A61K 31/05
USPC ................................. 514/555, 565
See application file for complete search history.

(56) References Cited

U.S. PATENT DOCUMENTS 9,067,908 B2 *   6/2015   Delaire .................. A61K 8/375

FOREIGN PATENT DOCUMENTS

| CH | WO 2007096078 A1 * | 8/2007 | ............. A61K 31/05 |
| IN | WO 2011104667 A1 * | 9/2011 | ........... C07C 229/26 |

OTHER PUBLICATIONS

Yar et al., "The effects of resveratrol on cyclooxygenase-1 and -2, nuclear factor kappa beta, matrix metalloproteinase-9, and sirtuin 1 mRNA expression in hearts of streptozotocin-induced diabetic rats", 2011, Genet. Mol. Res., 10(4), pp. 2962-2975.*
Vallianou et al., "Resveratrol and Diabetes", 2013, The Review of Diabetic Studies, 10(4), pp. 236-242.*
Dolinsky et al., "Resveratrol prevents hypertension and cardiac hypertrophy in hypertensive rats and mice", 2013, Biochimica et Biophysica Acta, 1832(10), pp. 1723-1733.*

* cited by examiner

*Primary Examiner* — My-Chau T Tran
(74) *Attorney, Agent, or Firm* — Partners Law Group, Inc; Steve P. Hassid

(57) ABSTRACT

Methods of increasing the plasma concentration of resveratrol in a mammal in need thereof by administering to a mammal in need thereof an effective amount of trans-resveratrol and arginine for a period of at least two weeks.

9 Claims, 21 Drawing Sheets

FIG. 1

UC Davis Capsules
Certificate of Analysis Lot# 030512

*DESCRIPTION*
98% trans-resveratrol capsules for use as a dietary supplement.

*MANUFACTURE DATE*　　　　　　　　　　　　March 2012

| SPECIFICATIONS | | ANALYSIS |
|---|---|---|
| Chemical Classification | Organic, Nutritive | Organic, Nutritive |
| Physical Classification | Caps | Caps |
| Color | White Opaque Caps | White Opaque Caps |
| Odor | Characteristic | Characteristic |
| Taste | None | None |
| Active Ingredients: | | |
|   Trans-resveratrol (mg/cap) | 45 | 45 |
| Inactive Ingredeints: | | |
|   Cellulose SC-90 (mg/cap) | 279 | 279 |
|   Magnesium Stearate (mg/cap) | 5 | 5 |
| Heavy Metals: | | |
|   Pb (ppm) | Less than 0.5 | 0.25 |
|   Hg (ppm) | Less than 0.2 | Complies |
|   Cd (ppm) | Less than 5 | Complies |
| Microbiological Assays: | | |
|   Total Plate Count (CFU/g) | Less than 1000 | 100 |
|   Yeast and Mold (CFU/g) | Less than 100 | 10 |
|   E. Coli (CFU/g) | Negative | Complies |
|   Salmonella (CFU/g) | Negative | Complies |
|   Staph. aureus (CFU/g) | Negative | Complies |
| Pesticide Assays: | | |
|   Organochlorine | Negative | Complies |
|   Organophosphorous | Negative | Complies |
|   Organonitrigen | Negative | Complies |
|   N-Methyl Carbamates | Negative | Complies |
| Aflatoxins | Negative | Complies |
| Country of Origin | USA | |
| Country of Shipment | USA | |
| Shelf Life | 5 years when stored in tightly closed dark containers in a cool dry location. Limit exposure to air. | |
| Expiration Date | March 2017 | |

FIG. 2

ResArgin™
UC Davis Capsules
Certificate of Analysis Lot# 030112

*DESCRIPTION*
ResArgin™ is a proprietary (patent pending) trans-resveratrol arginine conjugate for use as a dietary supplement.

*MANUFACTURE DATE*      March 2012

| SPECIFICATIONS | | *ANALYSIS* |
|---|---|---|
| Chemical Classification | Organic, Nutritive | Organic, Nutritive |
| Physical Classification | Caps | Caps |
| Color | White Opaque Caps | White Opaque Caps |
| Odor | Characteristic | Characteristic |
| Taste | None | None |
| Active Ingredients: | | |
|   Trans-resveratrol (mg/cap) | 45 | 45 |
|   Arginine (mg/cap) | 40 | 40 |
| Inactive Ingredients: | | |
|   Cellulose SC-90 (mg/cap) | 235 | 235 |
|   Magnesium Stearate (mg/cap) | 90 | 90 |
| Heavy Metals: | | |
|   Pb (ppm) | Less than 0.5 | 0.25 |
|   Hg (ppm) | Less than 0.2 | Complies |
|   Cd (ppm) | Less than 5 | Complies |
| Microbiological Assays: | | |
|   Total Plate Count (CFU/g) | Less than 1000 | 100 |
|   Yeast and Mold (CFU/g) | Less than 100 | 10 |
|   E. Coli (CFU/g) | Negative | Complies |
|   Salmonella (CFU/g) | Negative | Complies |
|   Staph aureus (CFU/g) | Negative | Complies |
| Pesticide Assays: | | |
|   Organochlorine | Negative | Complies |
|   Organophosphorous | Negative | Complies |
|   Organonitrigen | Negative | Complies |
|   N-Methyl Carbamates | Negative | Complies |
| Aflatoxins | Negative | Complies |
| Country of Origin | USA | |
| Country of Shipment | USA | |
| Shelf Life | 5 years when stored in tightly closed dark containers in a cool dry location. Limit exposure to air. | |
| Expiration Date | March 2017 | |

FIG. 3

| Resveratrol Conjugates Mean Plasma PK Parameters-Oral Pharmacokinetics Studies in Rat (0.25 mM/Kg) | | | | | |
|---|---|---|---|---|---|
| Parameters | Resveratrol | Resveratrol-Succinate | Resveratrol-Citrulline | Resveratrol+Arginine (Physical mixture) | Resveratrol-Arginine Conjugate (ResArgin ™) |
| Dose (mM) | 0.25 | 0.25 | 0.25 | 0.25 | 0.25 |
| Cmax (nM) | 1712 | 6746 | 10485 | 1625 | 11289 |
| Tmax (h) | 0.25 | 0.25 | 0.25 | 0.50 | 0.25 |
| AUClast (hr*nmol) | 3817 | 7541 | 8656 | 4667 | 17947 |
| AUCinf (hr*nmol) | 6562 | 11034 | 10126 | 5733 | 24008 |
| AUC % Extrap (%) | 27 | 9.7 | 7.7 | 18.5 | 9.0 |
| t1/2 (h) | 3.3 | 2.1 | 3.1 | 2.6 | 1.8 |
| MRT last (h) | 2.2 | 2.1 | 1.1 | 2.39 | 1.6 |

FIG. 4

| Resveratrol Conjugates -Oral PK in SD Rats (0.25 mM/Kg) | | | | | | | | |
|---|---|---|---|---|---|---|---|---|
| Summary of Resveratrol Plasma Concentrations (nM) | | | | | | | | |
| Time (h) | Resveratrol | | | Resveratrol - ArgininePhysical Mixture | | | Resveratrol-Arginine Conjugate (ResArgin ™) | | |
| | Mean | ± | Stdv | Mean | ± | Stdv | Mean | ± | Stdv |
| 0 | 0 | ± | 0 | 0 | ± | 0 | 0 | ± | 0 |
| 0.25 | 1712 | ± | 383 | 1228 | ± | 522 | 11289 | ± | 2990 |
| 0.50 | 1542 | ± | 417 | 1625 | ± | 771 | 8042 | ± | 1476 |
| 1 | 823 | ± | 321 | 926 | ± | 274 | 5785 | ± | 1049 |
| 2 | 720 | ± | 248 | 901 | ± | 263 | 3070 | ± | 1405 |
| 4 | 405 | ± | 136 | 712 | ± | 127 | 1246 | ± | 252 |
| 6 | 305 | ± | 66 | 281 | ± | 31 | 674 | ± | 158 |
| 24 | 0 | ± | 0 | 0 | ± | 0 | 0 | ± | 0 |

FIG. 8

|  | 1 hr | 2 hr |
|---|---|---|
| Age | 60.31 ± 0.81 | 60.14 ± 1.19 |
| Weight (kg) | 66.98 ± 1.96 | 64.93 ± 2.23 |
| BMI (kg/m2) | 24.89 ± 0.67 | 23.87 ± 0.66 |
| Waist Circumference (cm) | 73.74 ± 1.96 | 71.24 ± 2.29 |
| SBP (mm Hg) | 123.58 ± 2.40 | 121.36 ± 3.59 |
| DBP (mm Hg) | 72.58 ± 1.60 | 77.74 ± 1.72 |
| Heart Rate (beats/minute) | 66.15 ± 1.51 | 68.5 ± 2.08 |
| MAP (mm Hg) | 89.58 ± 1.68 | 92.28 ± 2.25 |
| Fasting Glc (mg/dL) | 94.31 ± 0.92 | 98.86 ± 1.96 |
| Total Chol (mg/dL) | 214.47 ± 5.48 | 208 ± 6.79 |
| HDL Chol (mg/dL) | 70.14 ± 3.42 | 71.86 ± 5.30 |
| LDL Chol (mg/dL) | 124.53 ± 3.84 | 120.76 ± 5.16 |
| TG (mg/dL) | 98.86 ± 10.10 | 76.86 ± 10.89 |

FIG. 18

| Agonist | Outcome | trans-res baseline | trans-res 1 hr | p | ResArg baseline | ResArg 1 hr | p |
|---|---|---|---|---|---|---|---|
| 1 μL collagen | Max aggregation (Ω) | 5.5 (4,8) | 6 (3.5, 6.5) | ns | 6 (5, 8) | 6 (5, 7) | ns |
| | Slope | 7 (6.5, 8.5) | 7 (6.5, 7.5) | ns | 7.5 (6.5, 8.5) | 7 (5.5, 8) | 0.030 |
| | Lag (second) | 105 (80.5, 123) | 111.5 (90, 134) | 0.008 | 94 (83.5, 117.5) | 98.5 (89, 143.5) | 0.004 |
| | AUC | 17.4 (11.75, 23.15) | 16.6 (12.35, 21.25) | ns | 19.45 (15.45, 27.4) | 19.2 (11.05, 21.8) | ns |
| 5 μL collagen | Max aggregation (Ω) | 9 (5.5, 11) | 7.5 (4.5, 9.5) | ns | 9 (6.5, 11.5) | 7.5 (5.5, 11) | ns |
| | Slope | 8 (6.5, 9.5) | 7.5 (6.5, 9) | ns | 8.5 (7.5, 9.5) | 8 (7, 9.5) | ns |
| | Lag (second) | 75 (63.5, 95.5) | 74 (64, 97.5) | ns | 75 (58.5, 91) | 73 (61.5, 97) | ns |
| | AUC | 30.05 (18.65, 35.65) | 25.05 (14.85, 31.5) | ns | 28.5 (19.4, 36.45) | 24.05 (16.65, 38.85) | ns |
| 10 μL ADP + Chronolume | Max aggregation (Ω) | 10 (8.5, 15) | 10 (7.5, 13) | ns | 12 (9.5, 13.5) | 11 (9, 14) | ns |
| | Slope | 8.5 (6, 11.5) | 6.5 (5.5, 8) | 0.008 | 8 (7, 16) | 7 (6, 9) | 0.014 |
| | Lag (second) | 33 (28, 39) | 36 (30, 42) | ns | 34.5 (28, 40) | 33.5 (29.5, 39) | ns |
| | AUC | 39.3 (29.4, 54.25) | 36.35 (30.45, 46.45) | ns | 42.7 (34.8, 49.3) | 38.5 (31, 51.1) | ns |
| | ATP (nmole) | 0.6 (0.41, 1.1) | 0.585 (0.31, 0.77) | ns | 0.49 (0.36, 0.695) | 0.57 (0.385, 0.93) | ns |
| 10 μL AA | Max aggregation (Ω) | 7.5 (5.5, 9.5) | 6.5 (5.5, 7.5) | ns | 8.5 (7, 10.5) | 6.5 (3.5, 8.5) | 0.041 |
| | Slope | 6 (5, 7.5) | 5.5 (4, 6.5) | ns | 6 (5, 8) | 5.5 (4.5, 7.5) | ns |
| | Lag (second) | 33 (21, 42) | 30.5 (19, 42) | ns | 27 (18, 42.5) | 34.5 (24, 49.5) | ns |
| | AUC | 30.1 (23.8, 39.75) | 27.6 (18, 30.65) | ns | 33.5 (27.1, 40.8) | 25.65 (22.6, 39) | 0.005 |

FIG. 19

| Resveratrol Conjugates Mean Plasma PK Parameters-Oral Pharmacokinetics Studies in Rat (0.25 mM/Kg) | | | | | | |
|---|---|---|---|---|---|---|
| | GATEWAY CONJUGATES | | | | SIRTRIS FORMULATIONS* | |
| Parameters | Resveratrol | Resveratrol-Succinate | Resveratrol-Citrulline | Resveratrol-Arginine Conjugate | Formulation 10 | Formulation 15 |
| Dose (mM) | 0.25 | 0.25 | 0.25 | 0.25 | 0.438 | 0.438 |
| Cmax (nM) | 1712 | 6746 | 10485 | 11289 | 7416 | 4671 |
| Tmax (h) | 0.25 | 0.25 | 0.25 | 0.25 | 0.08 | 0.14 |
| AUClast (hr*nmol) | 3817 | 7541 | 8656 | 17947 | 8258 | 6261 |
| AUCinf (hr*nmol) | 6562 | 11034 | 10126 | 24008 | 9547 | 6879 |
| AUC % Extrap (%) | 27 | 9.7 | 7.7 | 9.0 | | |
| t1/2 (h) | 3.3 | 2.1 | 3.1 | 1.8 | 2.16 | 1.73 |
| MRT last (h) | 2.2 | 2.1 | 1.1 | 1.6 | 3.47 | 2.89 |

FIG. 20

| Sl.No. | Resveratrol Conjugates | Solubility (ug/mL) |
|---|---|---|
| 1 | Resveratrol | 39.5 |
| 2 | Resveratrol-Arginine (ResArgin) | 915 |
| 3 | Resveratrol-Citrulline | >15000 |
| 4 | Resveratrol-Serine | >50000 |
| 5 | Resveratrol-Valine | >50000 |

METHODS AND COMPOSITIONS FOR IMPROVING MICROVASCULAR FUNCTION, SUPPRESSING CYCLOOXYGENASE ACTIVITY, REDUCING PLATELET AGGREGATION AND INCREASING LEVELS OF RESVERATROL IN PLASMA

BACKGROUND OF THE INVENTION

Field of the Disclosure

The present disclosure generally relates to methods and compositions that involving resveratrol, which has been studied for its ability to reduce cardiovascular diseases. The present disclosure is on methods and compositions involving trans-resveratrol and arginine, which provides a variety of benefits and advantages, including but not limited to a more bio-available and bio-active form of trans-resveratrol. The present disclosure also includes data from a study that demonstrates that, when compared to other forms of trans-resveratrol, trans-resveratrol and arginine, provides various benefits and advantages, including but not limited to, improving the absorption of resveratrol, increasing the amount of resveratrol in plasma levels, improving microvascular function, reducing platelet aggregation, suppressing cyclooxygenase activity, reducing platelet aggregation and increasing levels of resveratrol in plasma.

General Background

Cardiovascular disease (hereafter, "CVD") is a leading cause of mortality in the United States and other industrialized nations [1, 2]. Therefore, simple and effective methods to reduce risk of CVD are important for both personal and public health strategies. Evidence from epidemiological investigations suggests that consumption of plant-based foods and products rich in polyphenolic compounds can have cardioprotective effect [3-5]. Among the polyphenols, a number of compounds have been suggested to have cardioprotective effects, including flavano-3-ols from cocoa [6], epigallocatechin gallate (hereafter, "EGCG") from green tea [7], and resveratrol, a phenolic compound found in grapes, red wine, purple grape juice, and some berries [8].

Resveratrol (3,5,4'-trihydroxystilbene) is a polyphenol, a stilbenoida derivating from stilbene and is produced in plants. Resveratrol was first isolated in 1940 from the roots of *Veratrum grandiflorum*, and then in 1963 resveratrol from *Polygonum cupsidatum*, a plant that is used in traditional Chinese and Japanese medicine [9, 10]. However, resveratrol was overlooked by the Western cultures until 1992 when it was suggested to be an explanation for the "French Paradox", an observation of lower rates of CVD in the French population, which was attributed to higher red wine consumption [9]. The optimal health benefit derived from red wine is achieved at a consumption of more than five glasses a day for longer period, which would be considerably more expensive than a resveratrol pill.

Resveraltrol was found well tolerated both in humans and animals. Resveratrol is non-genotoxic, non-mutagen, and has no reproductive toxicity. Usual human dose is 0.8-33 mg/kg, bw/day, while animal studies revealed no toxicity effect even at the dose of 500 mg/kg, bw/day for 3 months dosing [11-13]. Two structural isomers of resveratrol can be found in foods, cis- and trans- [8, 9]. The trans- form can undergo isomerisation to the cis- form when exposed to ultraviolet irradiation [14]. Trans-resveratrol (hereafter, "trans-res") is biologically active and the predominant form found in nature, and it is the isomer has been used in supplements and clinical interventions [15], due to instability of the cis isomer [8]. (FIG. 1 shows the composition of trans-res capsule). The naturally occurring amount of resveratrol in most foods is very low. Thus, even though it can cause an effect in a relatively short period of time, obtaining biologically active amount of resveratrol via diet alone is difficult. Illustrative of this, typical daily intakes of resveratrol from dietary sources are in the range of six to eight mg [16], while the amount of resveratrol supplementation in humans that has been reported to result in increased brachial artery flow mediated dilatation (hereafter, "FMD"; a measure of vascular function) on an acute basis is 30 to 270 mg [17].

Although resveratrol demonstrated to have beneficial effects under experimental conditions, most of its effects in humans are limited by its fast metabolism and low plasma exposure. Resveratrol undergoes rapid metabolism in intestines and liver resulting in poor plasma exposure [18, 19]. Resveratrol is rapidly absorbed, and depending on the dose, reaches maximum peak plasma concentration anywhere from 30 min to two hours after intake [15, 20]. Absorbed resveratrol is rapidly metabolized to conjugates of sulfate and glucuronide, and the metabolites appear to be quickly cleared from circulation [8, 15, 21].

Despite its rapid absorption and metabolism, supplemental resveratrol can have positive effects on a number of cardiovascular health outcomes, including endothelial function, platelet function, and blood lipids [15, 22]. An enhanced FMD response was reported with resveratrol supplementation as low as 10 mg per day for three months [23], as well as 75 mg for six weeks [24]. Reduction in low density lipoprotein (hereafter, "LDL") cholesterol was shown after daily intake of 8 mg of resveratrol for six months [25], while a decrease in total cholesterol was observed after supplementation of 250 mg for three months [26]. Daily supplementation with 8 mg of resveratrol for six months, followed by 16 mg per day for additional six months, resulted in a significant decrease in plasminogen activator inhibitor type 1 (hereafter, "PAI-1"), which is known to promote hemostasis [27], and is secreted by activated endothelial cells [28].

Resveratrol has been extensively studied for its potential to improve health and longevity. Prospective benefits of resveratrol supplementation have led to annual sales of more than $30 million in the United States in 2010. However, resveratrol is very expensive and limits the use of high dose. The inventions of the present disclosure provide an improved form of resveratrol which provides benefits including but not limited to improved bioavailability and pricing [29, 30].

A novel resveratrol-arginine conjugate (hereafter, "ResArgin™"; was provided by Gateway Health Alliances, Inc. Fairfield, Calif., hereafter, "Gateway". ResArgin™ composition is shown in FIG. 2. As part of the present disclosure, ResArgin™ was studied in rats, demonstrating, among other things, higher peak plasma levels and total plasma levels for a longer period of time when compared to trans-res and two other resveratrol conjugates: resveratrol-citrulline and resveratrol-succinate [31]. (See FIG. 3)

Additional experiments were done to assess, among other things, the bioavailability and bioactivity of ResArgin™ among postmenopausal women, a population at risk for cardiovascular disease [32]. The study determined, among other things, whether ResArgin™ intake would improve vascular function and compared those results to those of trans-res. The study also determined whether ResArgin™ improves measures of platelet function more than trans-res. Lastly, the study analyzed whether plasma resveratrol levels would be greater with ResArgin™ supplementation when compared to trans-res and that the level of improvement would be unexpected and related to the magnitude of change in the markers of vascular function and platelet function.

SUMMARY

Brief Description of Drawings

The drawings disclose illustrative embodiments and represent graphical summaries of the data explained and described herein. They do not set forth all embodiments. Other embodiments may be used in addition or instead. Details that may be apparent or unnecessary may be omitted to save space or for more effective illustration. Conversely, some embodiments may be practiced without all of the details that are disclosed. When the same numeral appears in different drawings, it is intended to refer to the same or like components or steps.

The above-mentioned features and objects of the present disclosure will become more apparent with reference to the following description taken in conjunction with the accompanying drawings and in which:

FIG. 1 lists the composition of trans-res capsule used in the experiments and studies discussed herein.

FIG. 2 lists the composition of ResArgin™ in the capsule used in the experiments and studies discussed herein.

FIG. 3 is a table which graphically compares ResArgin™ with other resveratrols in other pharmacokinetic rat studies. The result demonstrates that ResArgin™ had higher levels of plasma concentration when compared to other indicated resveratrols.

FIG. 4 is a table which graphically compares ResArgin™ with other resveratrols in other pharmacokinetic rat studies. The result demonstrates that ResArgin™ resulted in higher plasma concentration of resveratrol when compared to other indicated resveratrols.

FIG. 8 is a table which describes the baseline characteristics of study participants. Values are presented as mean±standard error of the mean (hereafter, "SEM"); 1 hr, one hour study; 2 hr, two hour study; BMI, body mass index; SBP, systolic blood pressure; DBP, diastolic blood pressure; MAP, mean arterial pressure; Glc, glucose; Chol, cholesterol; HDL, high density lipoprotein; LDL, low-density lipoprotein; TG, triglyceride.

FIG. 18 describes the changes in platelet function for intake of both ResArgin™ and trans-res. The results revealed a significant increase in lag time one-hour post consumption with both treatments when platelets were stimulated with 1 µL, collagen. Also, a significant decrease in slope was seen one hour after consumption of ResArgin™, but not for the trans-res group. Stimulation with 5 µL collagen showed no significant changes in either group. Significant decreases in maximum aggregation and area under the curve were observed one hour after intake of ResArgin™ when platelets were stimulated with 10 µL arachidonic acid, but no changes were noted in the trans-res group. Lumi-aggregometry with 10 µL ADP revealed a significant decrease in slope one-hour post consumption of both trans-res and ResArgin™. Values are presented as median (interquartile range). ADP=adenosine diphosphate; AA=Arachidonic acid; Max aggregation=maximum aggregation; AUC=area under the curve; ns=not significant. p<0.05 represent statistically significant difference between the baseline measurement and the 1-hour post-consumption of the assigned treatment (n=31). Statistical analysis was performed using non-parametric Friedman's 2-way ANOVA by ranks test.

FIG. 19 is a table which compares resveratrol conjugates with two Sirtris formulations. Sirtris is a GSK Company, data is from patent WO 2009/089011 A2; units of the parameters normalized for comparative purpose. The results demonstrate that ResArgin™ from Gateway had higher Cmax (11289 nM) than Sirtris formulations (7416 nM and 4671 nM).

FIG. 20 is a bar chart which compares ResArgin™ among other resveratrol in terms of aqueous solubility. The result demonstrates that ResArgin™ improved its solubility.

METHODS

The study was a randomized, controlled, double-blind, crossover trial that postmenopausal women were randomly assigned to consume 90 mg of ResArgin™ or trans-res, in a crossover design, at least one week apart, after an overnight fast. The study included two separate investigations: a one hour study and a two hour study (FIG. 1). Based on the results, dosage of 10 mg to 5000 mg ResArgin or trans-res daily for a period of at least two weeks are expected to have identical results. The one hour study assessed changes in select outcomes 30 minutes and one hour post-consumption of the resveratrol treatments. The two hour study was designed to fully assess and compare the responses to trans-res and ResArgin™.

Results

A more rapid and pronounced response from ResArgin™ than trans-res on markers of microvascular function. The changes noted were significantly associated with plasma resveratrols levels. At one hour, significant increases RHI and FRHI. Significant reductions in platelet reactivity under certain test conditions were noted at one hour after ResArgin™ intake, but not for trans-res.

Plasma resveratrol levels were significantly increased 30 and 60 min after the consumption of both ResArgin™ and trans-res, but the levels were only correlated with RHI and FRHI in the ResArgin™ group.

DETAILED DESCRIPTION

Participants of Study

Healthy postmenopausal women ages 50 to 70 years of age were recruited from the greater Sacramento area via email and newspaper advertisements. Postmenopausal status was defined as the cessation of the menses for at least one year, and a level of follicular stimulating hormone (hereafter, "FSH") of 23-116.3 mIU/mL. All women were non-smokers, had no history of chronic disease, had no allergies to fruits, and did not regularly use any medications except thyroid medications. Use of dietary supplements other than standard multivitamin/mineral formulas (supplying up to 100% daily value) was an exclusion factor. Eligibility was determined by completion of a telephone interview, followed by a clinical screening visit conducted at the UC Davis Ragle Human Nutrition Research Center, which included a peripheral arterial tonometry (hereafter, "PAT") measurement, comprehensive metabolic and lipid panels, and assessment of platelet function abnormalities as determined by platelet function analyzer-100 (PFA-100) closure time readings (94-193 sec).

Figure 7:
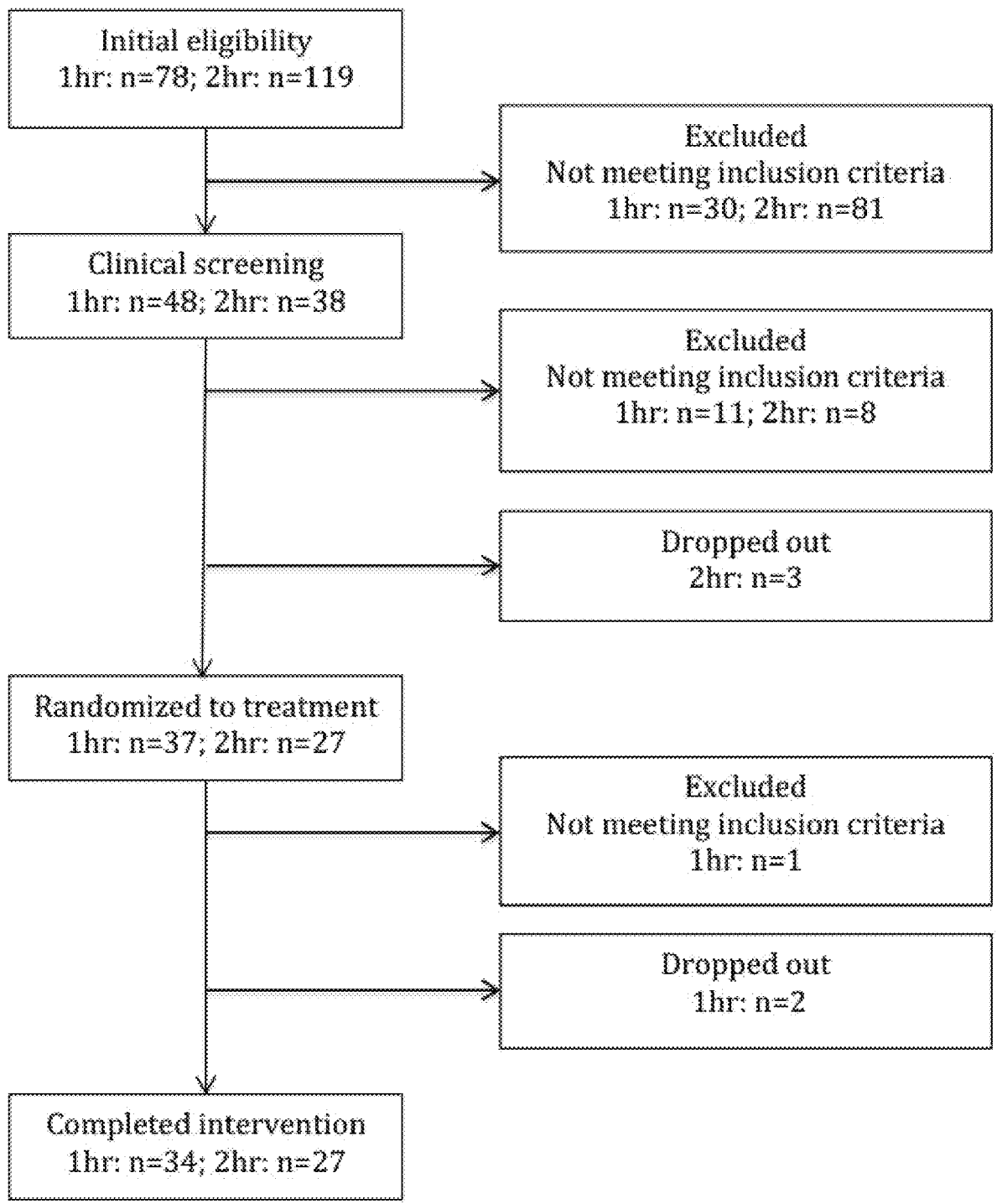
FIG. 7 is a flow chart that describes the number of the participants and process in each separate study discussed herein.

For the one hour study, 37 women were enrolled between March and October 2012, of which 34 finished (FIG. 7). The two hour study was conducted between June and November 2014, of which 27 women were enrolled and completed the study (FIG. 7).

The Institutional Review Board of the University of California, Davis approved the study protocol, and all participants provided written informed consent prior to enrollment.

Study Design

Figure 5:
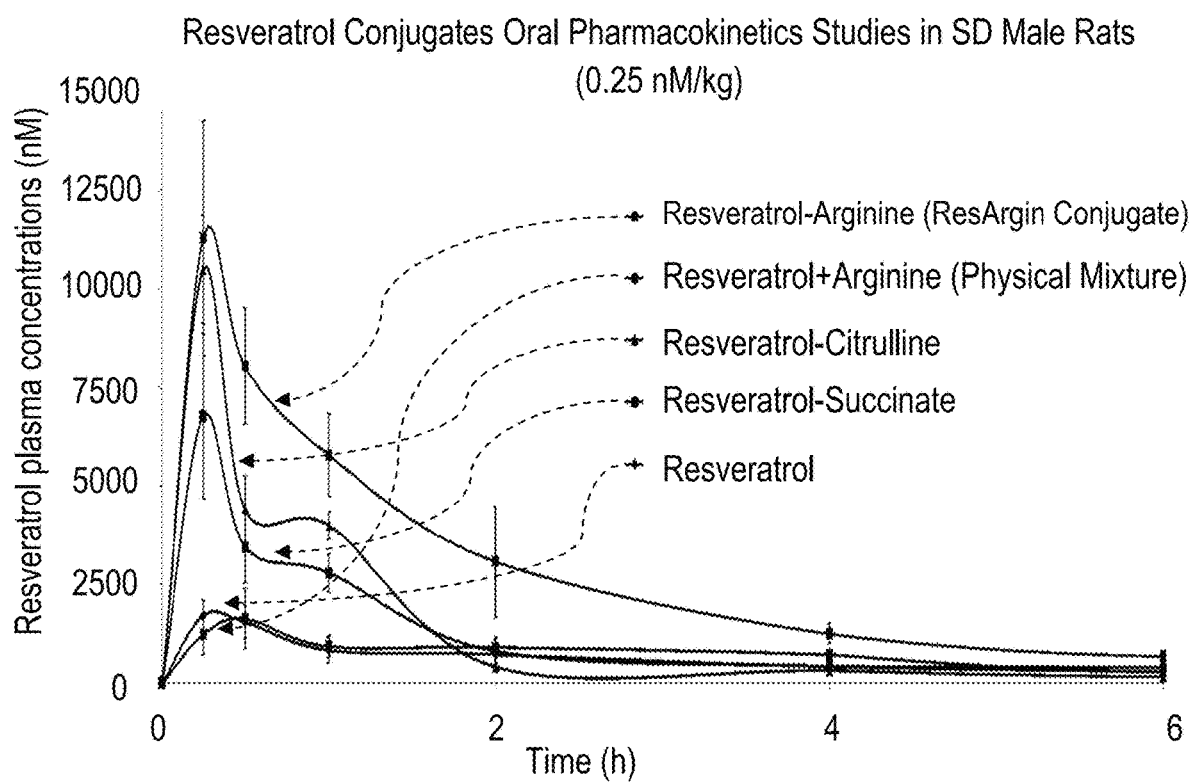
FIG. 5 is a line chart which demonstrates that ResArgin™ had higher plasma concentration and persisted for a longer period when compared to trans-resveratrol alone, a physical mixture of resveratrol and arginine, and two other resveratrol conjugates: resveratrol-citrulline and resveratrol-succinate.
Figure 6:
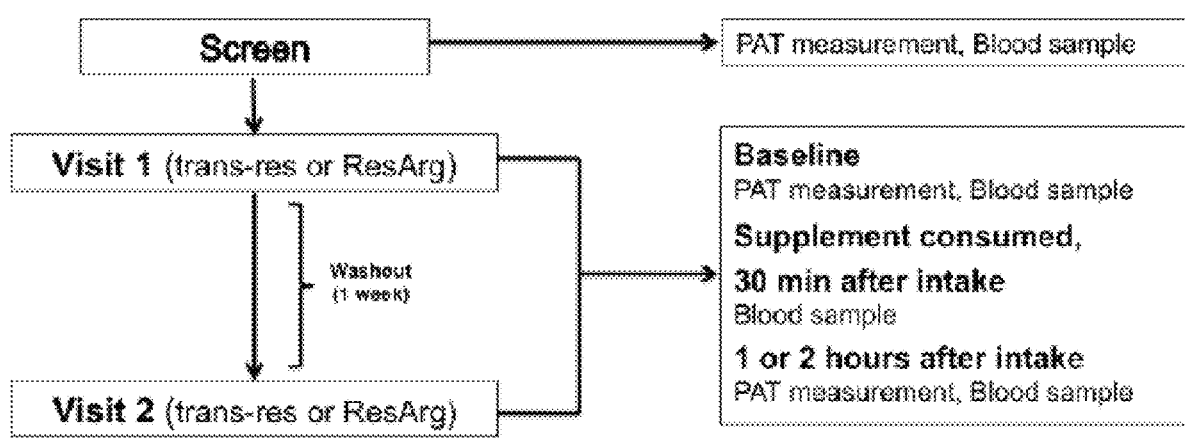
FIG. 6 is a flow chart that describes the process of the study discussed herein. 1 hr, one hour; 2 h, two hour.

Participants were randomized by block design to consumed trans-res or ResArgin™ in random order. Randomization was performed by the study coordinator following a predetermined plan formulated via a web-based random number generator. Both treatments contained 90 mg of trans-res, provided as two solid white, hard-shelled capsules (FIG. 1-5). The study included two separate investigations: a one hour study and a two hour study (FIG. 6). Baseline anthropometric and biochemical measures collected during test day one are listed in FIG. 8. During each study visit, which took place after an overnight fast, a baseline measurement of PAT and a blood sample were collected, followed by consumption of the assigned treatment. During the one hour study, PAT measurements and blood samples were collected thirty and sixty minutes after the capsules were consumed. During the two hour study, a PAT measurement and blood sample were taken two hours after the capsules were consumed.

All participants completed a three-day food record, which included two weekdays and a weekend day, one week prior to the first test day. For the duration of the study period, the participants were instructed to continue their normal dietary patterns while avoiding the intake of resveratrol-rich foods such as red wine, red grapes, peanuts and berries. Food records were analyzed using the Food Processor SQL software (version 10.1.0).

Data Analysis

All data are expressed as mean SEM, unless otherwise stated. Data were initially assessed for normality and outliers, and values not normally distributed, determined by the Shapiro-Wilk test, were transformed and rechecked for normality. Statistical analyses were conducted using univariate ANOVA with a Bonferroni post-hoc confidence interval or a paired t-test. Two variables were used: Treatment (trans-res and ResArgin™) and Time (0, 1 and/or 2 hours). For nonparametric data, changes from baseline and differences between the treatments were analyzed using Friedman's two-way analysis of variance by ranks with the Wilcoxon signed-rank post-hoc test and presented as medians (interquartile range). P-values of <0.05 were considered statistically significant. All analyses were performed with IBM SPSS software (version 22.0.0.0).

Metabolic Measurements

Blood samples were analyzed for a comprehensive metabolic panel, lipid panel, and complete blood count by the UC Davis Medical Center Department of Pathology.

Vascular Function

Microvascular function was assessed via PAT, using the Endo-PAT2000 (Itamar Medical Ltd., Caesarea, Israel) [33]. Briefly, prior to the PAT measurement, participants were acclimated to the controlled test room conditions by resting in a supine position for 30 minutes. A finger probe was then placed on the middle finger of both hands, and a blood pressure cuff was fitted on the forearm of the experimental arm (the non-dominant arm). The measurement was performed in a supine position with both arms supported at heart level. The procedure included five to ten minutes of baseline recording, followed by a five-minute occlusion period during which the blood pressure cuff was inflated approximately 60 mmHg above the individual's systolic blood pressure. After five minutes, the pressure was released and the resulting reactive hyperemia response recorded for an additional three to five minutes. The system software then automatically calculated three indices of microvascular function.

First, the reactive RHI was calculated, which is the ratio of the average of the pulse wave amplitude (hereafter, "PWA") during a one-minute period following one minute of reactive hyperemia to the average PWA during a 3.5-minute of baseline period. An increase in RHI indicates improvement of microvascular function. Second, the FRHI was calculated as the natural logarithmic transformation of the RHI ratio, without the baseline correction factor and utilizing only the readings from 90 to 120 seconds following the reactive hyperemia. Third, an augmentation index (hereafter, "AI") was calculated as a measure of arterial stiffness, which was considered along as well as normalized to a heart rate of 75 beats per minute (hereafter, "AI@75"). The AI and AI@75 are considered as supplementary measures of cardiovascular risk assessment, since an increase in AI represents an increase in cardiovascular risk [34].

One Hour Study

Figure 9:
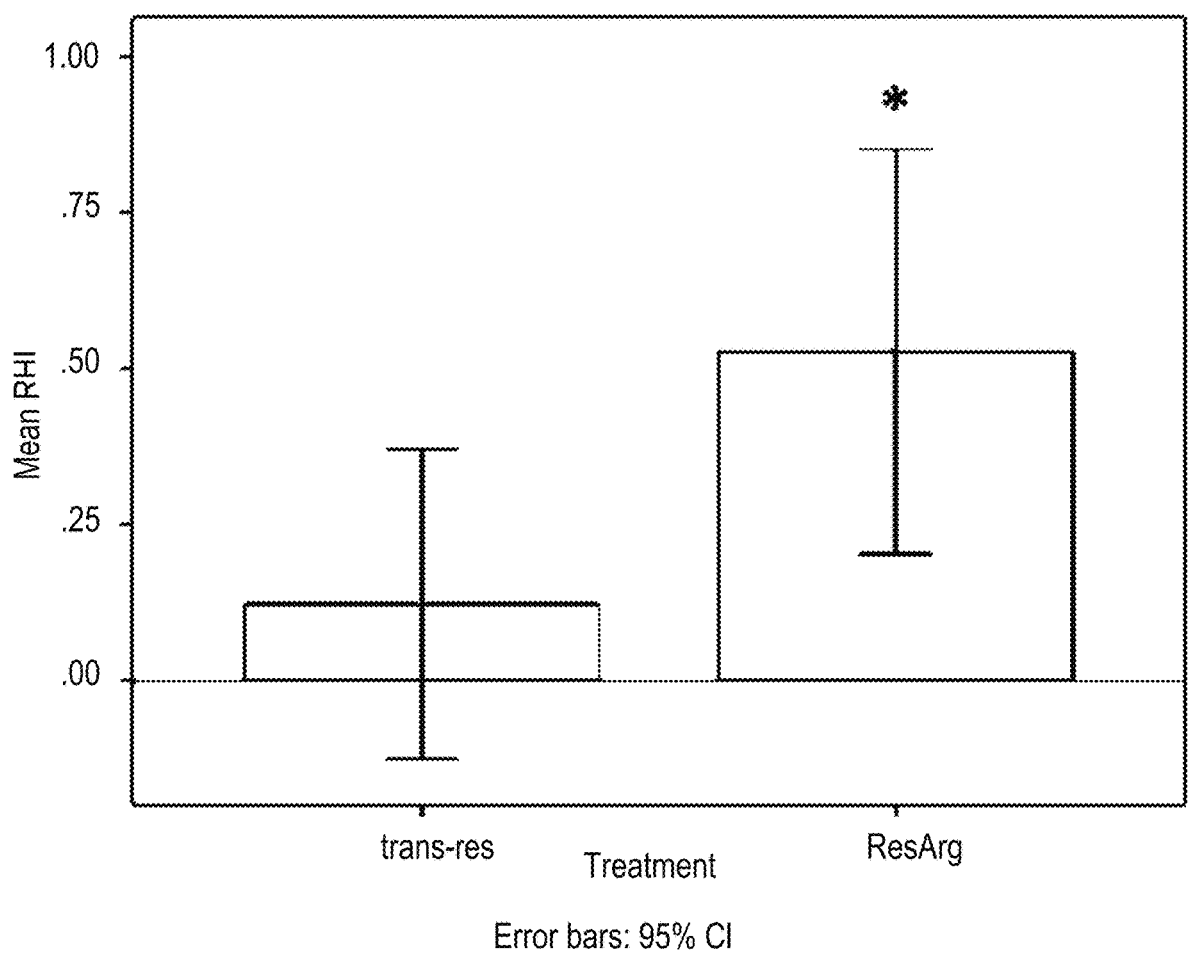
FIG. 9 is a bar chart which graphically describes the changes ($\Delta$=post−pre) in microvascular function (reactive hyperemia index, hereafter, "RHI"; also termed peripheral arterial tonometry index) for one hour study. The results demonstrates that change in RHI was significantly greater with ResArgin™ for one hour study (0.123±0.121 trans-res versus 0.527±0.158 ResArgin™, p=0.035). *p<0.05 difference between treatments. Statistical analysis was performed using paired t-test.
Figure 10:
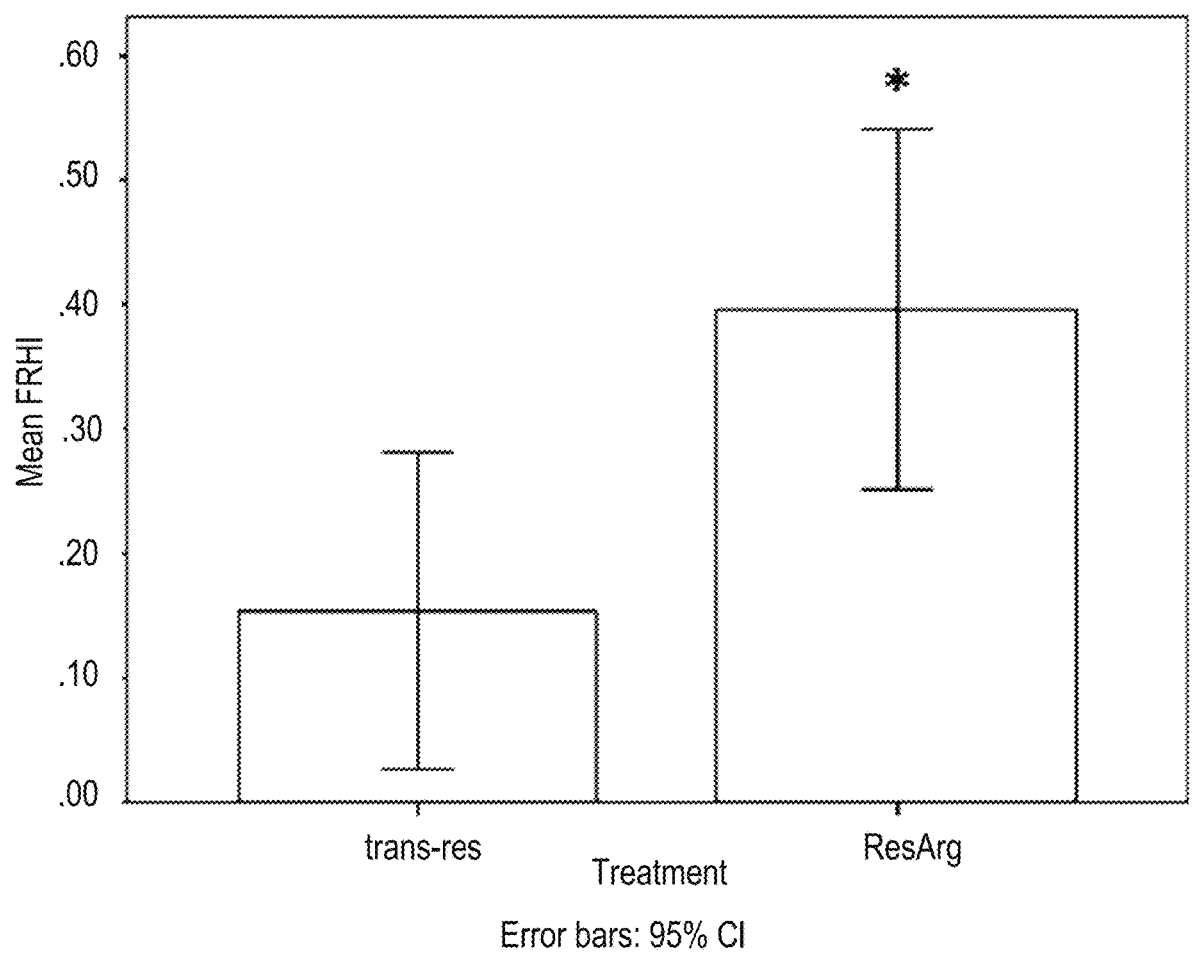
FIG. 10 is a bar chart which graphically describes the changes ($\Delta$=post−pre) in microvascular function (Framingham Reactive Hyperemia Index, hereafter, "FRHI") for one hour study. The results demonstrates that change in FRHI was significantly greater with ResArgin™ for one hour study (0.154±0.062 trans-res versus 0.396±0.070 ResArgin™, p=0.009). *p<0.05 difference between treatments. Statistical analysis was performed using paired t-test.

Changes (Δ=post−pre) in microvascular function for RHI and FRHI were significantly greater with ResArgin™ compared to trans-res (FIG. 9, 10). For RHI, change with ResArgin™ for 1 hour study (0.527±0.158, p=0.035) was significantly greater with trans-res (0.123±0.121, p=0.035). As for FRHI, change in ResArgin™ was also significantly greater than it in trans-res (0.306±0.173 versus −0.108±0.161; p>0.05).

Two Hour Study

Figure 11:
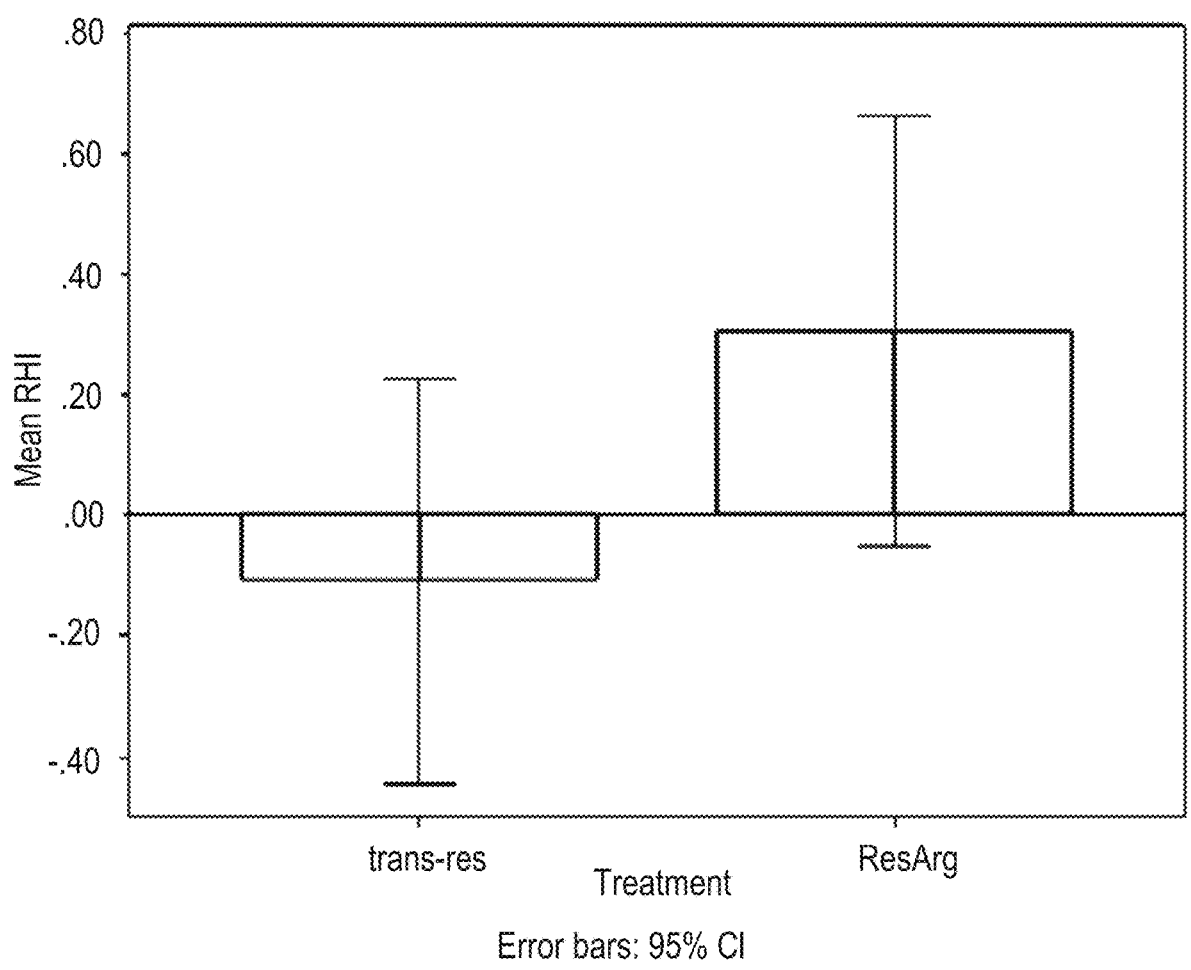
FIG. 11 is a bar chart which graphically describes the changes ($\Delta$=post−pre) in microvascular function (RHI) for two hour study. The results demonstrates that change in RHI was not significantly between treatments for two hour study (−0.108±0.161 trans-res versus 0.306±0.173 ResArgin™; p>0.05).
Figure 12:
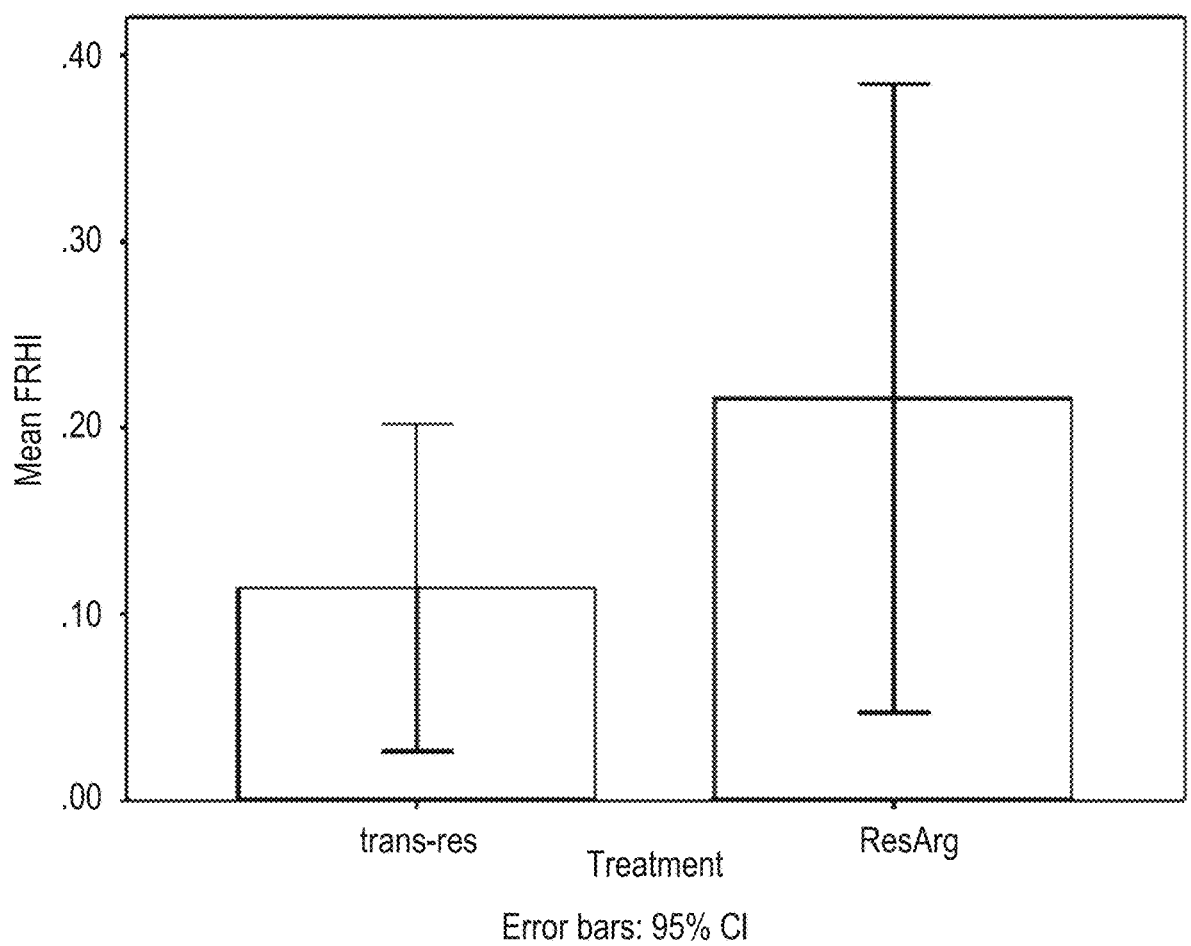
FIG. 12 is a bar chart which graphically describes the changes ($\Delta$=post−pre) in microvascular function (FRHI) for two hour study. The results demonstrates that change in FRHI was not significantly different between treatments for two hour study (0.113±0.042 trans-res versus 0.216±0.081 ResArgin™; p>0.05).

Changes (Δ=post−pre) in microvascular function were not significantly different between both treatments in RHI (−0.108±0.161 trans-res versus 0.306±0.173 ResArgin™; p>0.05). Similarly, changes in microvascular function were not significantly different between both treatments in FRHI (0.113±0.042 trans-res versus 0.216±0.081 ResArgin™; p>0.05) in the two hour study (FIG. 11, 12).

Combined Data

Figure 13:
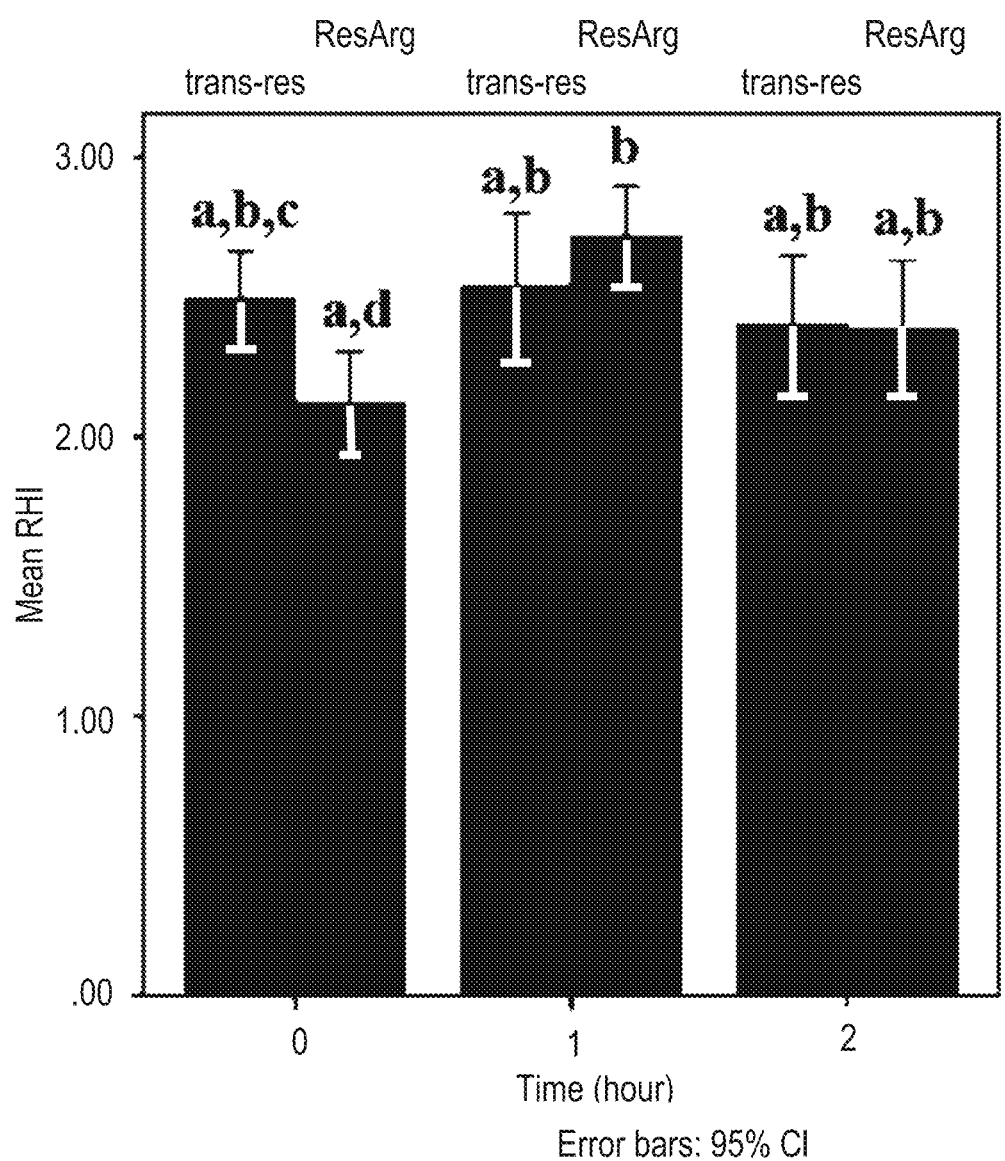
FIG. 13 is a bar chart which combines the data from one and two hour studies in changes of RHI. The result demonstrates that a significant improvement in RHI was seen one hour, but not two hours, after intake of ResArgin™ (2.119±0.085 at baseline versus 2.715±0.116 at 1 hour (p<0.0001) and 2.383±0.124 at 2 hours). a,b Values with different superscript letters are significantly different, p<0.05. Statistical analysis was performed using Univariate ANOVA with Bonferroni post hoc.
Figure 14:
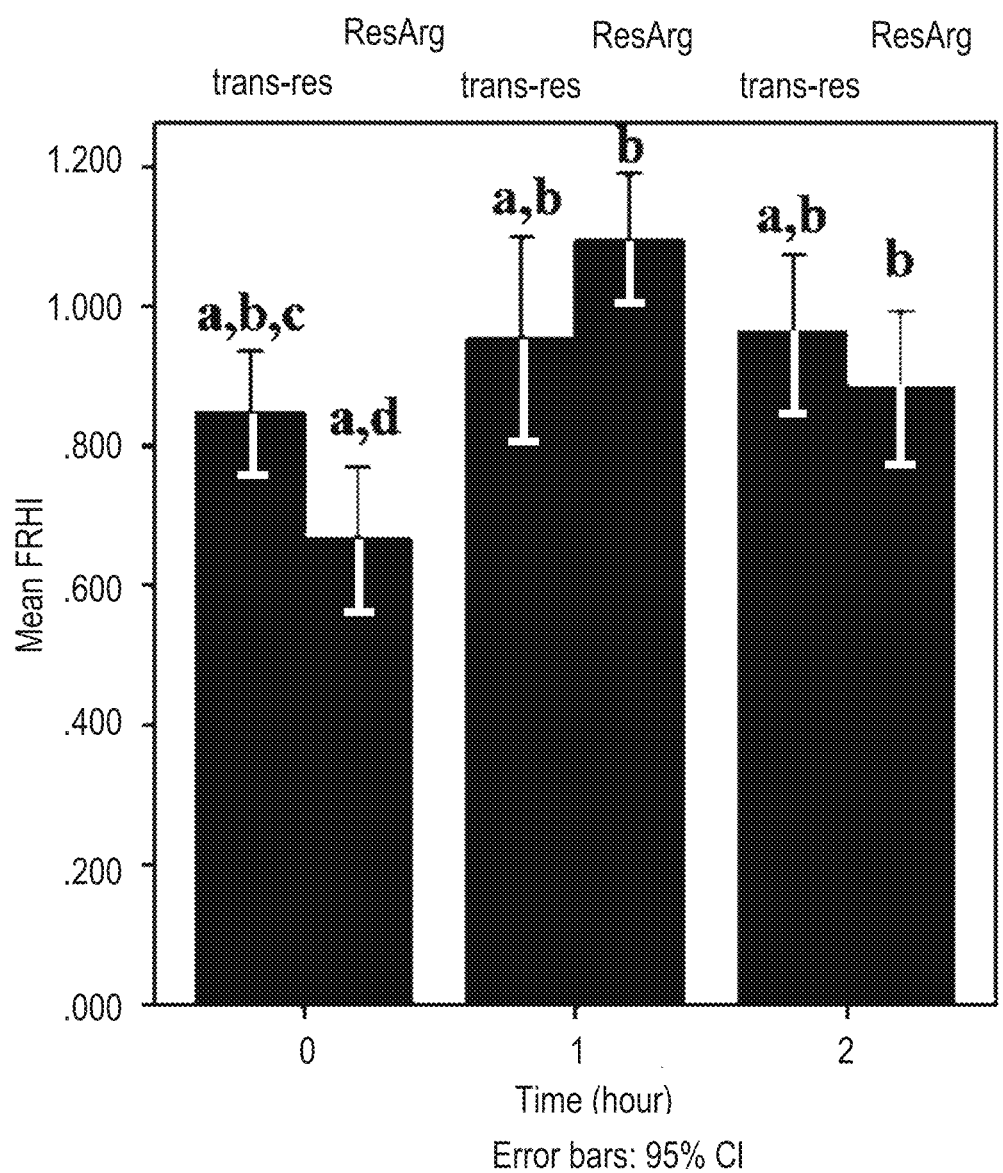
FIG. 14 is a bar chart which combines the data from one and two hour studies in changes of FRHI. The result demonstrates that a significant improvement in FRHI was seen one and two hours after intake of ResArgin™ (0.667±0.044 at baseline versus 1.095±0.061 at one hour (p<0.0001) and 0.882±0.065 at two hours (p=0.020). Additionally, the difference between one hour and two hours with ResArgin™ did not quite reach significance (p=0.052). No differences were observed with trans-res. a,b Values with different superscript letters are significantly different, p<0.05. Statistical analysis was performed using Univariate ANOVA with Bonferroni post hoc.

Univariate analysis revealed a significant interaction between treatment and time (p=0.020) for RHI. Further analysis showed a significant improvement in RHI one hour after intake of ResArgin™ (2.715±0.116, p<0.0001) compared to baseline (2.119±0.085) (FIG. 13), which was not observed with trans-res. Similarly, a significant treatment and time interaction was seen for FRHI at one hour for the ResArgin™ group compared to their baseline values (0.667±0.044), while no significant differences were noted in the trans-res group. Significant improvements in FRHI were seen one and two hours post-consumption of ResArgin™ (1.095±0.061, p<0.0001 and 0.882±0.065 p=0.020, respectively; FIG. 14), while no changes were noted for the trans-res group. The difference between one hour and two hour FRHI values with ResArgin™ showed a strong trend (p=0.052), while the difference did not quite reach significance. No significant changes were noted for AI or AI@75 in either group.

Plasma Resveratrol Concentrations

To assess bioavailability, plasma resveratrol levels were analyzed with a newly developed analytical method, because existing methods for measurement of resveratrol are focused on wine and other botanical sources and do not consider factors in plasma such as albumin. Plasma resveratrol concentrations were determined following analytical methods used to assess flavan-3-ols in human plasma following intake of a standardized cocoa extract [35]. Briefly, plasma was treated with acidified methanol [0.5% (v/v) of acetic acid in methanol; precooled to −20° C.] containing an appropriate recovery standard. The mixture was stored at −80 C for 12 hours to allow for cryo-assisted protein precipitation, and then centrifuged for 15 min at 16,500×g. The supernatant fraction was transferred and its volume reduced to less than 50 μL by removing the solvents under vacuum with a 7 SpeedVac Concentrator (Thermo Electron Corporation, Milford, Mass.). Fifty μL of acidified methanol was then added to the concentrated sample extracts, which were flushed with argon and stored at −80° C. until analysis using an Agilent high-pressure liquid chromatography (hereafter, "HPLC") 1100 series unit (Agilent Technologies, Santa Clara, Calif., USA). After thawing, 150 ul of HPLC grade water containing an appropriate internal standard was added to the samples.

Figure 15:
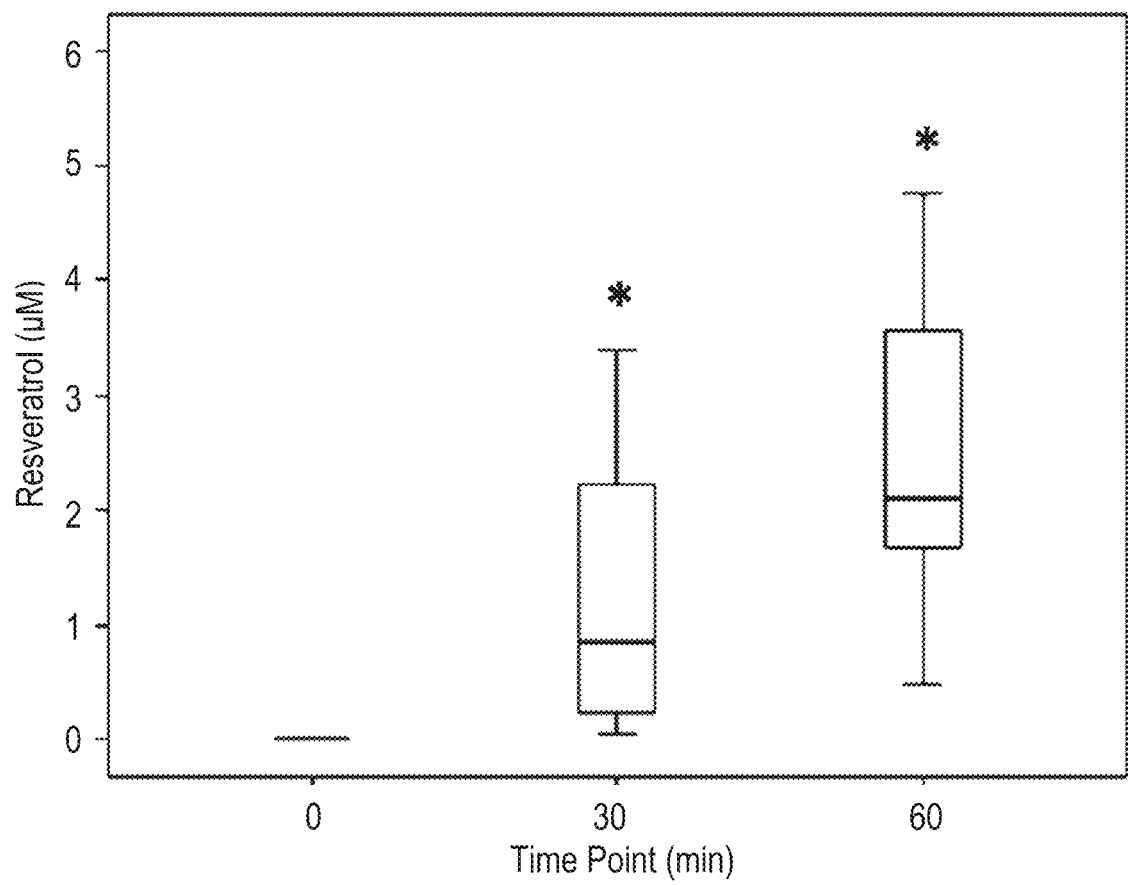
FIG. 15 is a bar chart which describes the changes in ResArgin™ plasma resveratrol contentration in one hour study. The result demonstrates that resveratrol plasma concentration significantly increased from baseline at 30 and 60 minutes after intake of ResArgin™ (0.00 (0.00, 0.00) at baseline versus 0.83 (0.21, 2.89) at 30 minutes versus 2.09 (1.60, 3.63) at 60 minutes; p<0.001). *p<0.05 compared to baseline. Statistical analysis was performed using non-parametric Friedman's 2-way ANOVA by ranks test (n=30). Values are presented as median (interquartile range).
Figure 16:
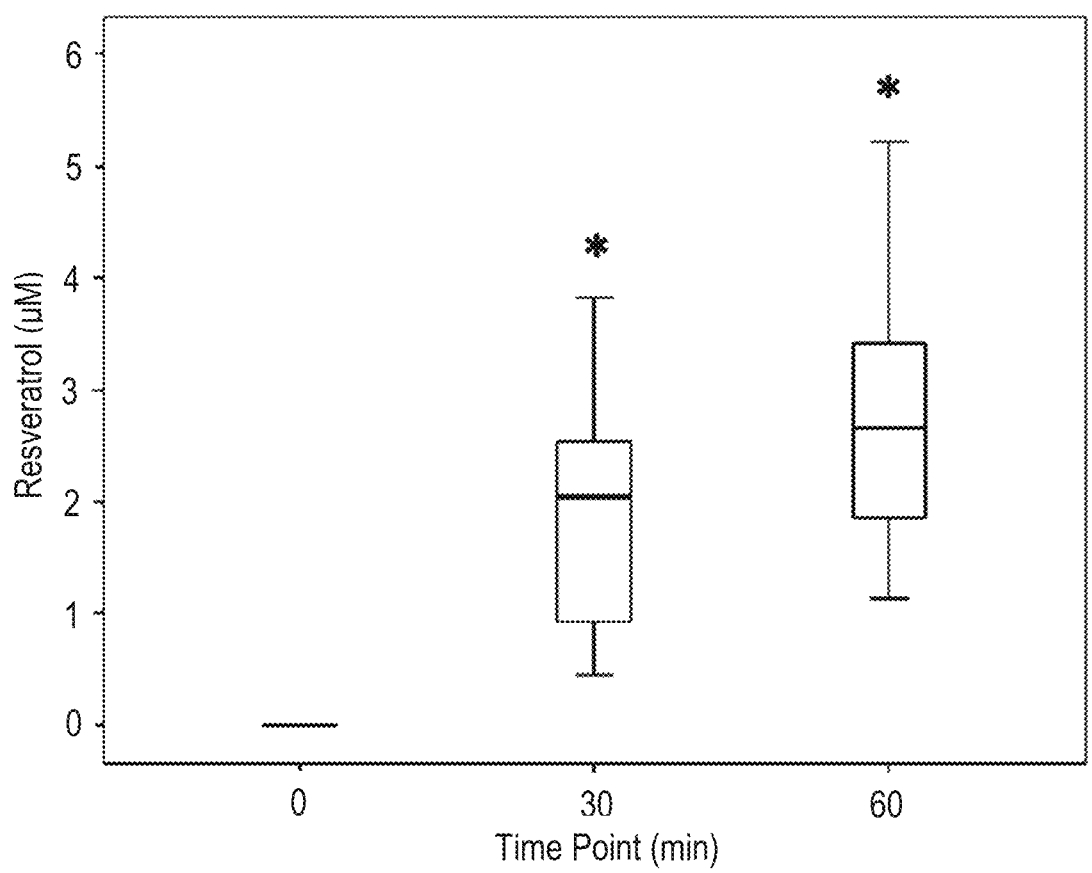
FIG. 16 is a bar chart which describes the changes in trans-res plasma resveratrol contentration in one hour study. The result demonstrates that resveratrol plasma concentration significantly increased from baseline at 30 and 60 minutes after intake of trans-res 0.00 (0.00, 0.00) at baseline versus 2.04 (0.82, 2.54) at 30 minutes versus 2.65 (1.69, 3.44) at 60 minutes; p<0.001). *p<0.05 compared to baseline. Statistical analysis was performed using non-parametric Friedman's 2-way ANOVA by ranks test (n=30). Values are presented as median (interquartile range).
Figure 17:
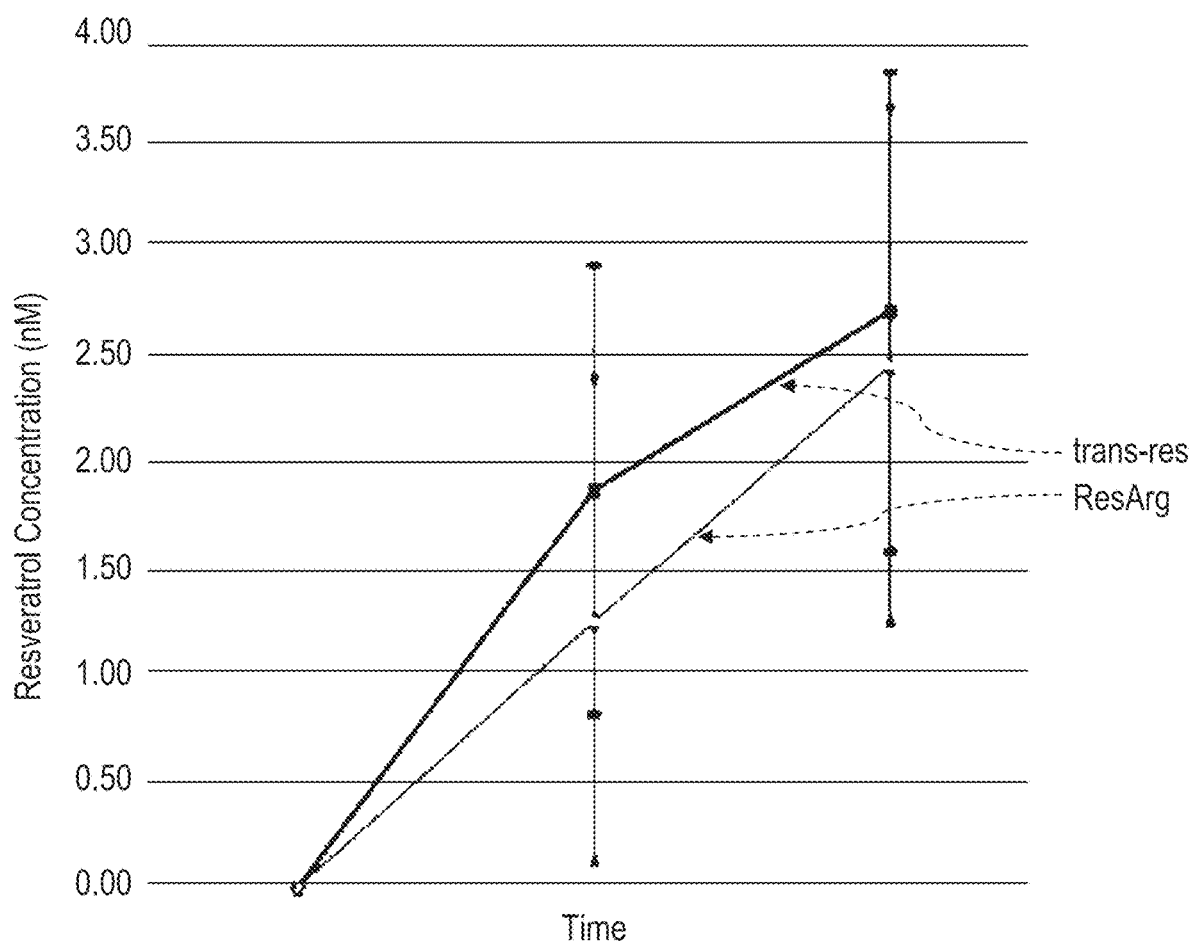
FIG. 17 is a line chart which graphically describes the changes in plasma resveratrol concentration for both ResArgin™ and trans-res. The result demonstrates that both treatments were not significantly different.
Figure 21:
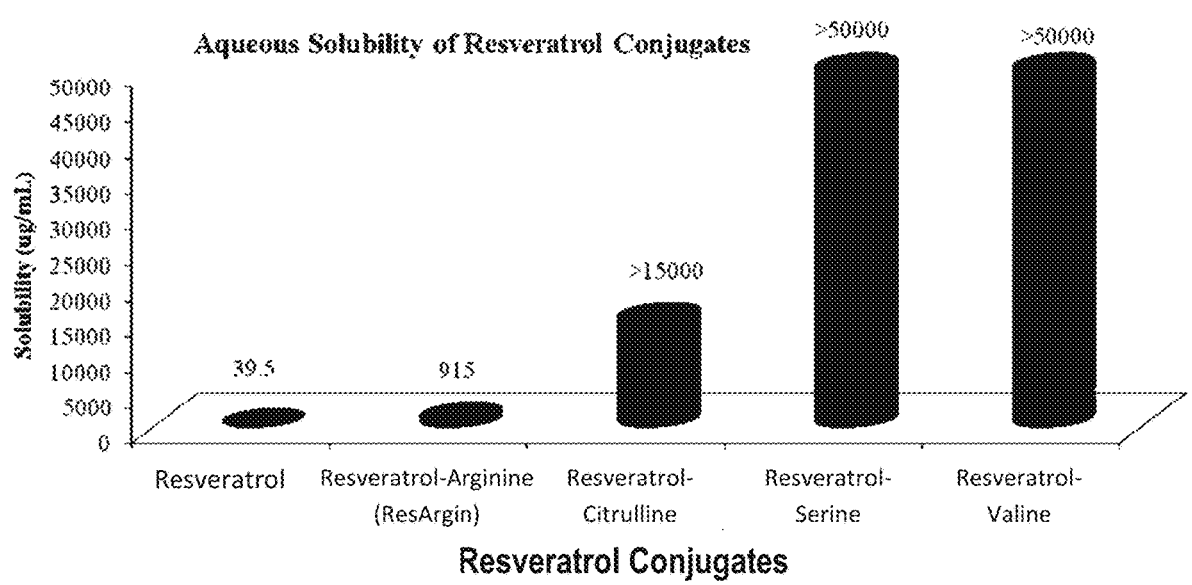
FIG. 21 is a bar chart which compares ResArgin™ among other resveratrol in terms of aqueous solubility. The result demonstrates that ResArgin™ improved its solubility.

The plasma resveratrol concentrations were not significantly different between ResArgin™ and trans-res. After intake of ResArgin™, plasma resveratrol concentration significantly changed from baseline ((0.00 (0.00, 0.00) to 30 minutes (0.83 (0.21, 2.89)) and 60 minutes (2.09 (1.60, 3.63); p<0.001; FIG. 15), as well as after trans-res intake (0.00 (0.00, 0.00)) at baseline versus 2.04 (0.82, 2.54) at 30 minutes versus 2.65 (1.69, 3.44) at 60 minutes; p<0.001; FIG. 16). Means line graph for the two treatment are shown below in FIG. 17.

Correlations

A significant positive correlation was noted between plasma resveratrol and RHI (rs=0.221; p=0.034) as well as FRHI (rs=0.348; p=0.001). Further analysis showed a significant correlation between plasma resveratrol and RHI and FRHI for ResArgin™ (rs=0.435; p=0.002 and rs=0.527; p<0.0001, respectively) but not between plasma resveratrol and RHI and FRHI for trans-res (rs=0.010; p=0.949 and rs=0.165; p=0.273, respectively).

Platelet Function

Platelet reactivity during clinical screening was assessed by a PFA-100 (Siemens, Deerfield, Ill.) [36], which measures platelet function by simulating arterial hemostasis under blood flow shear stress. During the intervention, platelet function was assessed by a whole blood/optical lumi-aggregometer (Chrono-log Model 700, Havertown, Pa.) [37, 38]. Briefly, platelet aggregation was measured via electrical impedance (or electrical resistance), whereas lumi-aggregometry was used to examine aggregation together with adenosine triphosphate (hereafter, "ATP") release, which is determined with firefly luciferin-luciferase system. For the impedance technique without ATP release, 500 μL, of each, saline and whole blood were added to a plastic cuvette and stirred at 1000 rpm. For the lumi-aggregometry procedure, 450 µL, saline, 450 µL, whole blood and 100 µL, of luciferin-luciferase reagent were added to a plastic cuvette and stirred at 1000 rpm. One of the following agonists was used to stimulate platelets: collagen (1 µL and 5 µL), AA (10 µL) or ADP (10 µL). ATP release was measured only when platelets were activated with ADP. The aggregation was measured over a period of six minutes, following the addition of an agonist.

Platelet function analysis revealed a significant increase in lag time one-hour post consumption with both treatments when platelets were stimulated with 1 µL collagen ($p=0.008$ for trans-res and $p=0.004$ for ResArgin™; FIG. 18). A significant decrease in slope was seen one hour after consumption of ResArgin™ ($p=0.004$; FIG. 18), but not for the trans-res group. Stimulation with 5 µL collagen showed no significant changes in either group. Lumi-aggregometry with 10 µL ADP revealed a significant decrease in slope one-hour post consumption of both trans-res and ResArgin™ ($p=0.008$ and $p=0.014$, respectively; FIG. 18). Significant decreases in maximum aggregation and AUC were observed one hour after intake of ResArgin™ when platelets were stimulated with 10 µL AA ($p=0.041$ and $p=0.005$, respectively; FIG. 18), but no changes were noted in the trans-res group.

Discussion

The present study assessed, among other things, the relative bioactivity and bioavailability of a supplemental ResArgin™ compared to trans-res, the form commonly used in most dietary supplements. The data supported improvements in microvascular function and platelet function with ResArgin™ which were likely correlated with increases in plasma resveratrol levels, while no effects were noted following intake of trans-res.

Resveratrol is reported to support endothelial nitric oxide synthase (hereafter, "eNOS") [39] and endothelial cell function. Endothelial dysfunction is an initial step in atherosclerosis [40], and is characterized by reduced nitric oxide (hereafter, "NO") bioavailability, an important vasodilator that is directly produced and released by endothelial cells [41, 42], which is involved in initiation and progression of atherosclerosis, a multifaceted condition resulting pathologies associated with CVD. Treatment of human umbilical vein endothelial cells with a physiological concentration of trans-res (1 µM) up-regulated the expression of eNOS [43], although cell culture models may not accurately reflect in vivo expression due to the lack of metabolites in the culture medium. Consequently, examining if supplementation with resveratrol can affect microvascular function and indicators of NO activity is important.

A number of investigations have been explored in a potential value of resveratrol supplementation on vascular function, since vasodilation is highly dependent on NO bioavailability. The measurement is primarily conducted by FMD, which assesses NO-mediated response in the conduit arteries of the peripheral circulation. However, evidence on this topic is conflicting. Supplementation with 600 mg of red grape extract led to a significant peak in FMD response 60 minutes post-consumption when compared to baseline measurements and a placebo [44]. It should be noted though, that in addition to 0.9 mg of trans-res the supplement evaluated in the above study contained an array of grape polyphenols, some in much higher concentrations than resveratrol (4.32 mg epicatechin, 2.72 mg catechin and 2.07 mg gallic acid), which may have contributed to the positive effects on endothelial relaxation. A recent publication that investigated the bioactivity of multiple supplements, including 100 mg of resveratrol, 800 mg each of green, black, and white tea extract, 250 mg of pomegranate extract, 650 mg of quercetin, 500 mg of acetyl-1-carnitine, 600 mg of lipoic acid, 900 mg of curcumin, 1 g of sesamin, 1.7 g of cinnamon bark extract, and 1.0 g fish oil for six months showed no significant change in FMD [45]. A study testing a supplement containing 100 mg of resveratrol combined with vitamin D3, quercetin and rice bran phytate and microencapsulated in plant starches and dextrins (Longevinex; Resveratrol Partners, LLC) for three months reported improvements in FMD [39]. Because vitamin D, quercetin, and rice bran phytates have positive effects on cardiovascular outcomes on their own [39], it is difficult to determine if the positive changes were due to resveratrol, synergism with other compounds, or the other compounds independent of the resveratrol. An intervention that examined the effects of a single dose or 30, 90, and 270 mg of trans-res one hour after consumption reported an increase in FMD with all three levels [17]. Wong et al. also reported that intake of 75 mg of trans-res led to a significant increase in FMD one hour post-consumption, as well as after daily intake for six weeks [24]. Similarly, a study that supplemented stable coronary artery disease patients with 10 mg of trans-res for three months demonstrated a significant improvement in FMD [23]. In contrast, a study that assessed microvascular function by PAT reported no significant changes in RHI (PAT index) 90 minutes after consumption of a supplement containing 1, 1.5 or 2 g of trans-res (data were combined from the three doses) that was served with a meal. However, a trend towards improvement ($p=0.06$) was seen in the RHI after four weeks of daily intake compared to the baseline visit [46]. A recent investigation reported no effect of daily intake of 250 mg of trans-res for eight weeks, but a positive effect in the control group [47]. Interestingly the same study reported that supplementation with trans-res abolished the positive effects of daily exercise on blood lipids [47].

The exemplary dose of resveratrol used in the present study (90 mg) was previously reported to induce positive effects on endothelial relaxation, measured by FMD, at one hour after intake [17]. This study has witnessed an improvement in changes of microvascular function (RHI), one hour after consumption of ResArgin™ but not with trans-res. Combined data from the one hour and two hour studies also revealed a significant improvement in the RHI one hour after intake. The change in RHI was not significantly different between the treatments at the two-hour time point, which suggests an acute response within one hour after intake of ResArgin™ that appears to diminish by two hours after intake. Analysis of FRHI data confirms this argument, since the change in FRHI was significantly greater with ResArgin™ at the one-hour time point, and not at two hours. Findings from this study are also in agreement with the previously mentioned investigation [46] that reported no significant changes in microvascular function measured by PAT acutely with unaltered trans-res.

In addition to microvascular function, a number of investigations have examined resveratrol bioavailability using a wide range of dosages, and inconsistent findings have been suggested as the reason for conflicting physiological responses [21]. Multiple factors are known to influence resveratrol bioavailability, including the food matrix, dose and physical properties of the molecule, all of which have the potential to alter maximal plasma concentration (hereafter, "Cmax") and the half-life [15, 21]. Efforts have been made in the past years to increase resveratrol bioavailability by enhancing the absorption rate and/or reducing intracellular metabolism to increase circulating levels of resveratrol [21]. For example, a recent study reported that intake of a 2 g lozenge containing 46% ribose, 46% of a fructose/sucrose mixture, and 8% trans-res led to a peak plasma concentration 15 minutes after consumption [48]. Evidence from this study showed that Cmax was achieved at an accelerated rate compared to previously reported averages at 30 minutes to two hours [20] for trans-res supplements. Two major limitations of this study are the small sample size and the lack of details regarding the plasma analysis methods. A study that supplemented healthy volunteers with a form of trans-res, where 40 g of resveratrol was solubilized in a lipid solution, led to a significantly higher Cmax when compared to trans-res alone [49]. However, it is unknown if a higher Cmax is related to clinical efficacy [21]. A recent report noted that supplementation with various doses of trans-res (0.073 mg to 5 g) also led to quick absorption and elevations of plasma resveratrol levels [15], but independent of clinical outcomes, it is difficult to interpret these results.

In another attempt to assess bioavailability, a significant increase in the urinary excretion of resveratrol metabolites was reported four hours, as well as 15 days, after intake of 187 mg of a beverage that contained 280 µg/L of hydroxycinnamic acids, 16 mg/L of anthocyanins, 96 mg/L of flavanols, 83 mg/L of hydroxybenzoic acids, and 5.7 mg/L of stilbenes, compared to baseline measurements or the control treatment [50]. Interestingly, this intervention also reported that sex might have an effect on bioavailability, as higher excretion of resveratrol metabolites were noted in women than men [50]. A previous intervention with postmenopausal women showed an increase in plasma resveratrol concentration after supplementation of 75 mg of trans-res for twelve weeks, although, no significant changes in plasma lipids or inflammatory markers, including C-reactive protein (hereafter, "CRP") and interleukin-6 (hereafter, "IL-6"), were noted [29].

Plasma resveratrol concentrations in the study were not significantly different between the two treatments at 30 and 60 minutes after intake. However, plasma resveratrol levels do not take into consideration that resveratrol might be present in various cells (e.g., erythrocytes) or tissues, and thus not measured in plasma [15, 21]. Additionally, the data showed an upward sloping curve for trans-res and ResArgin™ at 30 and 60 minutes, and it is unknown where the Cmax would have been achieved for each treatment. It is also unknown if Cmax or the area under the curve are the best indicators of bioavailability, and more studies are needed to clarify this issue.

A significant positive association is seen between plasma resveratrol and RHI, as well as FRHI. This finding is in agreement with the reported improvements in FMD related to an increase in plasma resveratrol concentrations [17]. Further analysis demonstrated that plasma resveratrol levels were not significantly correlated with RHI and FRHI following trans-res intake, but were significantly correlated between plasma resveratrol and RHI and FRHI following intake of ResArgin™.

One possible explanation for the improved bioactivity of ResAgr compared to trans-res would be a synergistic effect between resveratrol and arginine. It is unlikely that arginine alone was responsible for the positive effects, since the ResArgin™ supplement provided 80 mg of arginine, a relatively small amount compared to the reported improvements in vascular function with arginine supplementation, including two hours post-consumption of 15 g of L-arginine [51], and after daily intake of 21 g for three days [52]. However, the amount of arginine in ResArgin™ could have had an effect on the metabolism of ResArgin™, preserving resveratrol in a more bioactive form.

With respect to platelet function, since platelets are among the first to arrive at the site of endothelial activation [53]. But the evidence on the effects of resveratrol on platelet function is scarce. Moderate intake of red or white wine (300 mL/d) for 15 days resulted in an increase of resveratrol plasma levels, and a significantly higher release of NO by stimulated platelets [54]. Daily trans-res supplementation (10 mg) for three months significantly reduced platelet aggregation in stable coronary artery disease patients [23]. In vitro treatment of platelets with trans-res (10-1,000 µM) significantly reduced aggregation in a dose dependent fashion, while resveratrol supplementation (4 mg/kg/day) inhibited ADP-induced platelet aggregation in vivo in a hypercholesterolemic rat model [55]. Additional evidence from in vitro studies suggests that trans-res can inhibit cyclooxygenase (hereafter, "COX") activity and thus reduce platelet aggregation [56, 57]. Cyclooxygenase is an enzyme that converts AA to thromboxane A2 (hereafter, "TXA2"), and when this enzyme is inhibited, a significant reduction in platelet aggregation is noted [58]. Findings from our study are in agreement with the evidence on the effects of resveratrol on platelet function. The results showed that supplementation with ResArgin™ resulted in a significant decrease in maximal aggregation and AUC when platelets were stimulated with AA. This suggests that supplementation with ResArgin™ may have suppressed COX activity.

The study has certain limitations. Due to equipment or operator failure, the sample size that was originally estimated was not fully achieved, although a sufficient number of measurements were collected to obtain statistical significance. The study population of postmenopausal women, for whom age and postmenopausal status were risk factors for CVD, was unique, and it would be of interest to examine if similar effects would be seen in different at-risk populations such as overweight or obese adults or children, among those with diabetes, or smokers. Since only females were studied, findings are limited in making generalizations to men regarding bioavailability and bioactivity. Including multiple time points, both short-term and chronically, would better define the kinetics of the vascular response, platelet reactivity and plasma levels we observed. Additionally, examination of plasma NO bioavailability may provide a better understanding of changes in endothelial function seen with ResArgin™.

In conclusion, the data reports significant improvements in microvascular function when 90 mg of resveratrol was consumed as ResArgin™ but not as trans-res. The changes noted may have been significantly associated with plasma resveratrol levels. Lastly, AA induced platelet aggregation was reduced with ResArgin™ but not with trans-res. Collectively, evidence from this intervention suggests that supplementation with ResArgin™ might have greater cardioprotective benefits than trans-res.

REFERENCES

[1] Mozaffarian D, Benjamin E J, Go A S, et al. Heart Disease and Stroke Statistics-2015 Update: A Report From the American Heart Association. Circulation 2014.

[2] WHO. Global status report on noncommunicable diseases 20142014.

[3] Defago M D, Elorriaga N, Irazola V E, Rubinstein A L. Influence of Food Patterns on Endothelial Biomarkers: A Systematic Review. Journal of clinical hypertension (Greenwich, Conn.) 2014.

[4] Lopez-Garcia E, Hu F B. Nutrition and the endothelium. Current diabetes reports 2004; 4:253-9.

[5] Dauchet L, Amouyel P, Dallongeville J. Fruits, vegetables and coronary heart disease. Nature reviews Cardiology 2009; 6:599-608.

[6] Pucciarelli D L. Cocoa and heart health: a historical review of the science. Nutrients 2013; 5:3854-70.

[7] Bhardwaj P, Khanna D. Green tea catechins defensive role in cardiovascular disorders. Chinese journal of natural medicines 2013; 11:345-53.

[8] Delmas D, Aires V, Limagne E, et al. Transport, stability, and biological activity of resveratrol. Annals of the New York Academy of Sciences 2011; 1215:48-59.

[9] Artero A, Artero A, Tarin J J, Cano A. The impact of moderate wine consumption on health. Maturitas 2015; 80:3-13.

[10] Carrizzo A, Forte M, Damato A, et al. Antioxidant effects of resveratrol in cardiovascular, cerebral and metabolic diseases. Food and chemical toxicology: an international journal published for the British Industrial Biological Research Association 2013; 61:215-26.

[11] Cancer Epidemiol. Biomarkers Prev. 2007, 16, 1246-1252.

[12] Food and Chemical Toxicology. 2009, 47, 2170-2182.

[13] American Society for Nutritional Sciences, 2002, 257-260

[14] J. Agric. Food Chem. 1995, 43 (43), 281-283.

[15] Cottart C H, Nivet-Antoine V, Beaudeux J L. Review of recent data on the metabolism, biological effects, and toxicity of resveratrol in humans. Molecular nutrition & food research 2014; 58:7-21.

[16] Chachay V S, Kirkpatrick C M, Hickman I J, Ferguson M, Prins J B, Martin J H. Resveratrol—pills to replace a healthy diet? British journal of clinical pharmacology 2011; 72:27-38.

[17] Wong R H, Howe P R, Buckley J D, Coates A M, Kunz I, Berry N M. Acute resveratrol supplementation improves flow-mediated dilatation in overweight/obese individuals with mildly elevated blood pressure. Nutrition, metabolism, and cardiovascular diseases: NMCD 2011; 21:851-6.

[18] Drug Metabolism and Disposition, 2004, 32, 12, 1377-1382.

[19] Free Radical Biology & Medicine, 2002, 33, 387-39.

[20] Walle T. Bioavailability of resveratrol Annals of the New York Academy of Sciences 2011; 1215:9-15.

[21] Smoliga J M, Blanchard O. Enhancing the Delivery of Resveratrol in Humans: If Low Bioavailability is the Problem, What is the Solution? Molecules (Basel, Switzerland) 2014; 19:17154-72.

[22] Tome-Carneiro J, Larrosa M, Gonzalez-Sarrias A, Tomas-Barberan F A, Garcia-Conesa M T, Espin J C. Resveratrol and clinical trials: the crossroad from in vitro studies to human evidence. Current pharmaceutical design 2013; 19:6064-93.

[23] Magyar K, Halmosi R, Palfi A, et al. Cardioprotection by resveratrol: A human clinical trial in patients with stable coronary artery disease. Clinical hemorheology and microcirculation 2012; 50:179-87.

[24] Wong R H, Berry N M, Coates A M, et al. Chronic resveratrol consumption improves brachial flow-mediated dilatation in healthy obese adults. Journal of hypertension 2013; 31:1819-27.

[25] Tome-Carneiro J, Gonzalvez M, Larrosa M, et al. Consumption of a grape extract supplement containing resveratrol decreases oxidized LDL and ApoB in patients undergoing primary prevention of cardiovascular disease: a triple-blind, 6-month follow-up, placebo-controlled, randomized trial. Molecular nutrition & food research 2012; 56:810-21.

[26] Bhatt J K, Thomas S, Nanjan M J. Resveratrol supplementation improves glycemic control in type 2 diabetes mellitus. Nutrition research 2012; 32:537-41.

[27] Kishore P, Li W, Tonelli J, et al. Adipocyte-derived factors potentiate nutrient-induced production of plasminogen activator inhibitor-1 by macrophages. Science translational medicine 2010; 2:20ra15.

[28] Tanaka K A, Key N S, Levy J H. Blood coagulation: hemostasis and thrombin regulation. Anesthesia and analgesia 2009; 108:1433-46.

[29] Yoshino J, Conte C, Fontana L, et al. Resveratrol supplementation does not improve metabolic function in nonobese women with normal glucose tolerance. Cell metabolism 2012; 16:658-64.

[30] Semba R D, Ferrucci L, Bartali B, et al. Resveratrol levels and all-cause mortality in older community-dwelling adults. JAMA internal medicine 2014; 174:1077-84.

[31] Pharmacokinetic studies of various forms of resveratrol: Gateway Health Alliances, Inc.; 2010.

[32] Boukhris M, Tomasello S D, Marza F, Bregante S, Pluchinotta F R, Galassi A R. Coronary Heart Disease in Postmenopausal Women with Type II Diabetes Mellitus and the Impact of Estrogen Replacement Therapy: A Narrative Review. International journal of endocrinology 2014; 2014:413920.

[33] Kuvin J T, Patel A R, Sliney K A, et al. Assessment of peripheral vascular endothelial function with finger arterial pulse wave amplitude. American heart journal 2003; 146:168-74.

[34] Multi Function EndoPAT. Itamar Medical.

[35] Ottaviani J I, Momma T Y, Heiss C, Kwik-Uribe C, Schroeter H, Keen C L. The stereochemical configuration of flavanols influences the level and metabolism of flavanols in humans and their biological activity in vivo. Free radical biology & medicine 2011; 50:237-44.

[36] Kundu S K, Heilmann E J, Sio R, Garcia C, Davidson R M, Ostgaard R A. Description of an in vitro platelet function analyzer—PFA-100. Seminars in thrombosis and hemostasis 1995; 21 Suppl 2:106-12.

[37] Lohse J. Platelet function in obese children and adolescents. Hamostaseologie 2010; 30:S126-S31.

[38] Knoefler R, Siegert G, Kuhlisch E, Weissbach G. Diagnostics of Platelet Function Disorders by Lumi-Aggregometry—Results and Comparison of Methods. In: Scharrer I, Schramm W, eds. 34th Hemophilia Symposium: Springer Berlin Heidelberg; 2005:107-15.

[39] Fujitaka K, Otani H, Jo F, et al. Modified resveratrol Longevinex improves endothelial function in adults with metabolic syndrome receiving standard treatment. Nutrition research 2011; 31:842-7.

[40] Hansson G K, Hermansson A. The immune system in atherosclerosis. Nature immunology 2011; 12:204-12.

[41] Iantorno M, Campia U, Di Daniele N, et al. Obesity, inflammation and endothelial dysfunction. Journal of biological regulators and homeostatic agents 2014; 28:169-76.

[42] Kampoli A M, Tousoulis D, Antoniades C, Siasos G, Stefanadis C. Biomarkers of premature atherosclerosis. Trends in molecular medicine 2009; 15:323-32.

[43] Takizawa Y, Kosuge Y, Awaji H, et al. Up-regulation of endothelial nitric oxide synthase (eNOS), silent mating type information regulation 2 homologue 1 (SIRT1) and autophagy-related genes by repeated treatments with resveratrol in human umbilical vein endothelial cells. The British journal of nutrition 2013; 110:2150-5.

[44] Lekakis J, Rallidis L S, Andreadou I, et al. Polyphenolic compounds from red grapes acutely improve endothelial function in patients with coronary heart disease. European journal of cardiovascular prevention and rehabilitation: official journal of the European Society of Cardiology, Working Groups on Epidemiology & Prevention and Cardiac Rehabilitation and Exercise Physiology 2005; 12:596-600.

[45] Soare A, Weiss E P, Holloszy J O, Fontana L. Multiple dietary supplements do not affect metabolic and cardiovascular health. Aging 2014; 6:149-57.

[46] Crandall J P, Oram V, Trandafirescu G, et al. Pilot study of resveratrol in older adults with impaired glucose tolerance. The journals of gerontology Series A, Biological sciences and medical sciences 2012; 67:1307-12.

[47] Gliemann L, Schmidt J F, Olesen J, et al. Resveratrol blunts the positive effects of exercise training on cardiovascular health in aged men. The Journal of physiology 2013; 591:5047-59.

[48] Blanchard O L, Friesenhahn G, Javors M A, Smoliga J M. Development of a lozenge for oral transmucosal delivery of trans-resveratrol in humans: proof of concept. PloS one 2014; 9:e90131.

[49] Amiot M J, Romier B, Dao T M, et al. Optimization of trans-Resveratrol bioavailability for human therapy. Biochimie 2013; 95:1233-8.

[50] Rotches-Ribalta M, Urpi-Sarda M, Marti M M, Reglero G, Andres-Lacueva C. Resveratrol metabolic fingerprinting after acute and chronic intakes of a functional beverage in humans. Electrophoresis 2014; 35:1637-43.

[51] Lin C C, Tsai W C, Chen J Y, Li Y H, Lin L J, Chen J H. Supplements of L-arginine attenuate the effects of high-fat meal on endothelial function and oxidative stress. International journal of cardiology 2008; 127:337-41.

[52] Siasos G, Tousoulis D, Vlachopoulos C, et al. The impact of oral L-arginine supplementation on acute smoking-induced endothelial injury and arterial performance. American journal of hypertension 2009; 22:586-92.

[53] Massberg S, Brand K, Gruner S, et al. A critical role of platelet adhesion in the initiation of atherosclerotic lesion formation. The Journal of experimental medicine 2002; 196:887-96.

[54] Gresele P, Pignatelli P, Guglielmini G, et al. Resveratrol, at concentrations attainable with moderate wine consumption, stimulates human platelet nitric oxide production. The Journal of nutrition 2008; 138:1602-8.

[55] Wang Z, Huang Y, Zou J, Cao K, Xu Y, Wu J M. Effects of red wine and wine polyphenol resveratrol on platelet aggregation in vivo and in vitro. International journal of molecular medicine 2002; 9:77-9.

[56] Murias M, Handler N, Erker T, et al. Resveratrol analogues as selective cyclooxygenase-2 inhibitors: synthesis and structure-activity relationship. Bioorganic & medicinal chemistry 2004; 12:5571-8.

[57] Kutil Z, Temml V, Maghradze D, et al. Impact of wines and wine constituents on cyclooxygenase-1, cyclooxygenase-2, and 5-lipoxygenase catalytic activity. Mediators of inflammation 2014; 2014:178931.

[58] Li R, Diamond S L. Detection of platelet sensitivity to inhibitors of COX-1, P2Y(1), and P2Y(1)(2) using a whole blood microfluidic flow assay. Thrombosis research 2014; 133:203-10

We claim:

1. A method of improving microvascular function of a mammal in need thereof, the method comprising:
   providing to a mammal in need of improved microvascular function 10 mg to 5000 mg daily of a resveratrol and arginine conjugate;
   wherein the resveratrol and arginine conjugate increases the RHI of the mammal from about 0.369 to about 0.685 within about one hour of providing resveratrol and arginine conjugate to the mammal.

2. The method according to claim 1, wherein the effective amount of the resveratrol and arginine conjugate is 50 mg to 900 mg daily.

3. The method according to claim 1, wherein the effective amount of the resveratrol and arginine conjugate is 50 mg to 500 mg daily.

4. A method comprising:
   providing a mammal in need of improved microvascular function 10 mg to 5000 mg daily of a resveratrol and arginine conjugate for a period of at least two weeks;
   wherein the resveratrol and arginine conjugate increases the RHI of the mammal from about 0.369 to about 0.685 within about one hour of providing resveratrol and arginine conjugate to the mammal.

5. The method according to claim 4, wherein the effective amount of the resveratrol and arginine conjugate is 50 mg to 900 mg daily.

6. The method according to claim 4, wherein the effective amount of the resveratrol and arginine conjugate is 50 mg to 500 mg daily.

7. A method comprising:
   administering to a mammal in need of improved microvascular function within about an hour 10 mg to 5000 mg daily of a resveratrol and arginine conjugate for a period of at least two weeks;
   wherein the resveratrol and arginine conjugate increases the FRHI of the mammal from about 0.326 to about 0.466 within about one hour of providing resveratrol and arginine conjugate to the mammal.

8. The method according to claim 7, wherein the effective amount of the resveratrol and arginine conjugate is 50 mg to 900 mg daily.

9. The method according to claim 7, wherein the effective amount of the resveratrol and arginine conjugate is 50 mg to 500 mg daily.

* * * * *